(12) United States Patent
Sarioglu et al.

(10) Patent No.: US 12,370,548 B2
(45) Date of Patent: Jul. 29, 2025

(54) MICROFLUIDIC ANTIBODY MICROARRAY WITH AN ELECTRONIC SENSOR ARRAY

(71) Applicant: Georgia Tech Research Corporation, Atlanta, GA (US)

(72) Inventors: Ali Fatih Sarioglu, Atlanta, GA (US); Ruxiu Liu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1037 days.

(21) Appl. No.: 17/292,310

(22) PCT Filed: Nov. 11, 2019

(86) PCT No.: PCT/US2019/060747
§ 371 (c)(1),
(2) Date: May 7, 2021

(87) PCT Pub. No.: WO2020/097603
PCT Pub. Date: May 14, 2020

(65) Prior Publication Data
US 2021/0394182 A1 Dec. 23, 2021

Related U.S. Application Data

(60) Provisional application No. 62/758,104, filed on Nov. 9, 2018, provisional application No. 62/758,052, filed
(Continued)

(51) Int. Cl.
*B01L 3/00* (2006.01)
*B29C 33/38* (2006.01)
(Continued)

(52) U.S. Cl.
CPC ... *B01L 3/502761* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

2007/0111302 A1* 5/2007 Handique ............... B82Y 30/00
435/287.2
2009/0045333 A1* 2/2009 Chiarot .................. H01J 27/26
250/288
(Continued)

FOREIGN PATENT DOCUMENTS

| WO | 2012/094642 A2 | 7/2012 |
|---|---|---|
| WO | 2014/015333 A1 | 1/2014 |
| WO | 2017/070602 A1 | 4/2017 |

OTHER PUBLICATIONS

International Search Report mailed Aug. 6, 2020 for International Patent Application No. PCT/US2019/060747 (3 pages).
(Continued)

*Primary Examiner* — Michael P. Rodriguez
(74) *Attorney, Agent, or Firm* — Meunier Carlin & Curfman LLC

(57) ABSTRACT

Embodiments of the microfluidic device may include of an array of microfluidic cell capture chambers, each functionalized with a different antibody to recognize a target antigen, and a network of code-multiplexed Coulter counters placed at strategic nodes across the device to quantify the fraction of cell population captured in each microfluidic chamber. For example, an apparatus may comprise a fluid inlet port divided into a plurality of separate microfluidic paths, each separate microfluidic path configured to transport a plurality of cells, the plurality of separate microfluidic paths, each comprising a plurality of microfluidic cell capture chambers, an outlet port to discharge a merged output of cells from the plurality of microfluidic cell capture chambers, and a plu-
(Continued)

rality of sensors to detect cells passing into or out of a microfluidic cell capture chamber.

11 Claims, 38 Drawing Sheets

Related U.S. Application Data on Nov. 9, 2018, provisional application No. 62/758,025, filed on Nov. 9, 2018.

(51) Int. Cl.
| | | |
|---|---|---|
| *B29C 39/00* | (2006.01) | |
| *B29C 39/42* | (2006.01) | |
| *C23C 14/04* | (2006.01) | |
| *C23C 14/18* | (2006.01) | |
| *G01N 15/10* | (2024.01) | |
| *G01N 15/1404* | (2024.01) | |
| *G03F 7/00* | (2006.01) | |
| *B29K 105/00* | (2006.01) | |

(52) U.S. Cl.
CPC .... *B01L 3/502776* (2013.01); *B29C 33/3842* (2013.01); *B29C 39/006* (2013.01); *B29C 39/42* (2013.01); *C23C 14/042* (2013.01); *C23C 14/18* (2013.01); *G01N 15/1023* (2024.01); *G01N 15/1404* (2013.01); *G03F 7/0017* (2013.01); *B01L 2200/027* (2013.01); *B01L 2200/0652* (2013.01); *B01L 2200/12* (2013.01); *B01L 2200/16* (2013.01); *B01L 2300/0636* (2013.01); *B01L 2300/0819* (2013.01); *B01L 2300/0864* (2013.01); *B01L 2300/12* (2013.01); *B29K 2105/0002* (2013.01); *G01N 2015/1019* (2024.01)

(56) References Cited

U.S. PATENT DOCUMENTS

| | | | |
|---|---|---|---|
| 2011/0312518 A1* | 12/2011 | Davis | B01L 3/502761 |
| | | | 435/7.1 |
| 2014/0008307 A1 | 1/2014 | Guldiken et al. | |
| 2015/0210972 A1* | 7/2015 | Allbritton | C12M 23/12 |
| | | | 134/26 |
| 2015/0219592 A1* | 8/2015 | Goluch | G01N 27/413 |
| | | | 216/13 |
| 2016/0075987 A1 | 3/2016 | Zhang et al. | |
| 2016/0238623 A1 | 8/2016 | Sun et al. | |
| 2016/0377567 A1 | 12/2016 | Lu et al. | |
| 2019/0271634 A1 | 9/2019 | Handique | |
| 2021/0404937 A1 | 12/2021 | Sarioglu et al. | |

OTHER PUBLICATIONS

Written Opinion of the International Searching Authority mailed Aug. 6, 2020 for International Patent Application No. PCT/US2019/060747 (4 pages).

\* cited by examiner

MICROFLUIDIC ANTIBODY MICROARRAY WITH AN ELECTRONIC SENSOR ARRAY

STATEMENT REGARDING FEDERALLY SPONSORED RESEARCH

This invention was made with government support under Award No. 1752170 awarded by the National Science Foundation. The government has certain rights in the invention.

BACKGROUND

The present invention relates to a microfluidic antibody microarray, whose results are acquired by an integrated electrical sensor network, and methods of manufacturing same.

Cell surface markers are essential proteins or carbohydrates involved in a variety of cell functions, ranging from cell—cell interactions, ligand—receptor binding, and cell signaling, to serving as transporters, ion channels, enzymes, and adhesion molecules. Because different cell types usually express varying subsets of surface markers, cell surface markers, especially cluster of differentiation (CD) antigens, serve as chemical fingerprints to identify and classify cells (e.g., CD8 is a marker for cytotoxic T cell, a type of cancer-killer cell in the human immune system). Moreover, the expression of cell surface markers is dynamically altered at different stages during the differentiation of cell lineages, both for healthy cells and malignant tumor cells. For example, CD43 is expressed on the later stages of B cells but not on the earlier stages; the carcinoembryonic antigen is highly correlated to the development of colorectal cancer. The profiling of the cell surface markers, i.e., immunophenotyping, is, therefore, an important process with a wide range of applications in basic research and clinical studies to provide comprehensive information about the cell state and is routinely used to characterize cells in lineages of differentiation and to diagnose and classify diseases derived from those cells.

Currently, the gold standard for immunophenotyping assays is the flow cytometry, which can optically interrogate cells for target antigens. In flow cytometry, cells have to be first labeled with fluorophore-conjugated antibodies specifically targeting antigens of interest. Fluorescently labeled cells are then interrogated one by one as they flow through a detection zone, where fluorophores are excited by lasers, and the resulting fluorescence emission is measured by an array of photodetectors. From the fluorescence intensity, flow cytometers can quantify surface marker expression on cells and are therefore widely used for cell profiling in various research and clinical applications. On the other hand, a flow cytometer is usually limited in the number of antigens it can simultaneously probe due to overlap between excitation and emission spectra of different fluorophores. Moreover, flow cytometry cannot be performed at the point of care and has limited adoption beyond centralized laboratories due to bulky and expensive instrumentation that requires trained operators.

Microfluidic devices have also been used as immunoassays that can deterministically screen cell populations in a well-controlled microenvironment. Such devices rely on highly specific immunoaffinity-based capture of cells expressing target antigens and can be used to identify subpopulations in a microarray format. However, these assays mostly require external instrumentation such as a microscope for the readout, which negates the cost and portability benefits of the microfluidic chip itself. Stand-alone lab-on-a-chip assays that can quantitatively analyze cells can be built by integrating sensors into the microfluidic chip. Among various types of biosensors, Coulter counters are particularly attractive as they provide robust on-chip detection using simple electrodes that can easily be integrated into a microfluidic device. In fact, Coulter counters have been previously employed to quantify immunocapture of cells in a microfluidic chip by differentially counting cells at the inlet and outlet of the device. While providing an integrated solution, existing approaches are limited in their scalability to screen against multiple antibodies due to challenges 1) in integrating a large number of electrical sensors into the device without increasing device complexity and 2) in selective functionalization of different parts of the microfluidic device to create a multiplexed microarray format.

Accordingly, a need arises for techniques by which immunophenotyping of cell populations that may be performed at the point of care due to reduced size of equipment and reduced complexity of operation.

SUMMARY

Embodiments of the present systems and methods may provide immunophenotyping of cell populations that may be performed at the point of care due to reduced size of equipment and reduced complexity of operation.

Embodiments of the present systems and methods may provide a microfluidic antibody microarray, whose results are acquired by an integrated electrical sensor network, and methods of manufacturing same. Embodiments of the microfluidic device may include of an array of microfluidic cell capture chambers, each functionalized with a different antibody to recognize a target antigen, and a network of code-multiplexed Coulter counters placed at strategic nodes across the device to quantify the fraction of cell population captured in each microfluidic chamber. In embodiments, we interpret the electrical data providing cell capture statistics across the device in light of the specific antibody sequence each cell was subjected to, for calculating the prevalence of different subpopulations in a sample. Moreover, by electrically coding cell capture data, we compress the cell capture statistics across the whole device into a single electrical output without any information loss. Embodiments may use the device operation on a mixed population of different tumor cells. Embodiments may use the technique for identifying leukocyte subpopulations in a blood sample and benchmark the results against flow cytometry and a hematology analyzer on matched samples.

For example, in an embodiment, a method of fabricating a device may comprise fabricating a mold, forming a portion of the device using the mold, forming a plurality of ports in the molded portion of the device, fabricating an electrical sensor network on a glass substrate; and bonding the glass substrate to the molded portion of the device to form the device.

In embodiments, fabricating the mold may comprise patterning a silicon wafer using photolithography and treating a surface of the patterned silicon wafer to increase surface hydrophobicity for demolding. Treating the surface of the patterned silicon wafer may comprise treating the surface of the patterned silicon wafer with trichloro(octyl)silane for approximately 6 hours. Forming a portion of the device using the mold may comprise mixing a polydimethylsiloxane prepolymer and crosslinker, pouring the mixture on the mold, curing the polydimethylsiloxane, and peeling cured polydimethylsiloxane from the mold. The polydimethylsiloxane prepolymer and crosslinker may be mixed at approximately a 10:1 ratio. The method may further comprise degassing the poured mixture in vacuum, and the curing may be performed for approximately 4 hours in an oven at approximately 65° C. Forming the plurality of ports may comprise forming a fluidic inlet, outlet, and auxiliary functionalization ports with a biopsy punch. Fabricating the electrical sensor network may comprise forming a patterned photoresist on the glass substrate, evaporating chromium and then gold onto the patterned photoresist, and removing the patterned photoresist. The chromium may comprise a layer approximately 20 nm thick and gold may comprise a layer approximately 480 nm thick. The device may comprise a fluid inlet port divided into a plurality of separate microfluidic paths, each separate microfluidic path configured to transport a plurality of cells, the plurality of separate microfluidic paths, each comprising a plurality of microfluidic cell capture chambers, an outlet port to discharge a merged output of cells from the plurality of microfluidic cell capture chambers, a plurality of additional ports, and a plurality of sensors to detect cells passing into or out of a microfluidic cell capture chamber and the method may further comprise functionalizing a surface of each of the plurality of microfluidic cell capture chambers capture is functionalized by introducing one capture antibody into each microfluidic cell capture chamber through the plurality of additional ports.

In an embodiment, an apparatus may comprise a fluid inlet port divided into a plurality of separate microfluidic paths, each separate microfluidic path configured to transport a plurality of cells, the plurality of separate microfluidic paths, each comprising a plurality of microfluidic cell capture chambers, an outlet port to discharge a merged output of cells from the plurality of microfluidic cell capture chambers, and a plurality of sensors to detect cells passing into or out of a microfluidic cell capture chamber.

In embodiments, each of the plurality of microfluidic cell capture chambers may capture cells expressing target surface antigens. A surface of each of the plurality of microfluidic cell capture chambers capture may be functionalized by introducing one capture antibody into each microfluidic cell capture chamber. The apparatus may further comprise a plurality of additional ports configured to deliver the capture antibody exclusively to one microfluidic cell capture chamber. The apparatus may further comprise a plurality of additional ports configured to each receive a different capture antibody and to deliver each different capture antibody exclusively to one microfluidic cell capture chamber. Each microfluidic cell capture chamber may comprise a plurality of micropillars. Each micropillar may have a diameter of about 60 μm and a spacing of about 80 μm. The plurality of sensors may be Coulter sensors.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Embodiments of the present systems and methods may provide immunophenotyping of cell populations that may be performed at the point of care due to reduced size of equipment and reduced complexity of operation.

Embodiments of the present systems and methods may provide a microfluidic antibody microarray, whose results are acquired by an integrated electrical sensor network. Embodiments of the microfluidic device may include of an array of microfluidic cell capture chambers, each functionalized with a different antibody to recognize a target antigen, and a network of code-multiplexed Coulter counters placed at strategic nodes across the device to quantify the fraction of cell population captured in each microfluidic chamber, as shown, for example, in FIG. 1a. In embodiments, we interpret the electrical data providing cell capture statistics across the device in light of the specific antibody sequence each cell was subjected to, for calculating the prevalence of different subpopulations in a sample. Moreover, by electrically coding cell capture data, we compress the cell capture statistics across the whole device into a single electrical output without any information loss. Embodiments may use the device operation on a mixed population of different tumor cells. Embodiments may use the technique for identifying leukocyte subpopulations in a blood sample and benchmark our results against flow cytometry and a hematology analyzer on matched samples.

Figure 1A:
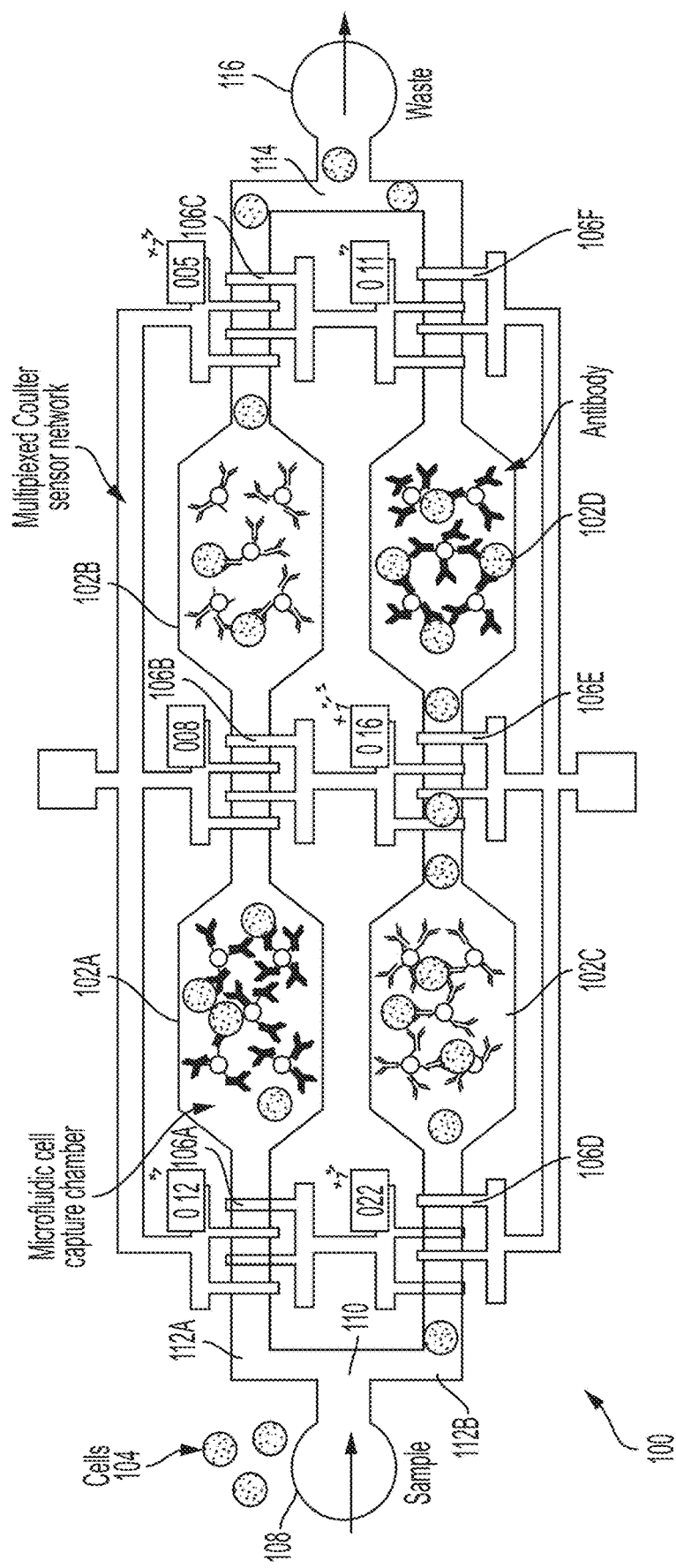
FIGS. 1a, 1b, 1c, and 1d illustrate an exemplary operation principle and design of an electronic antibody microarray, according to embodiments of the present devices and methods.
Figure 1B:
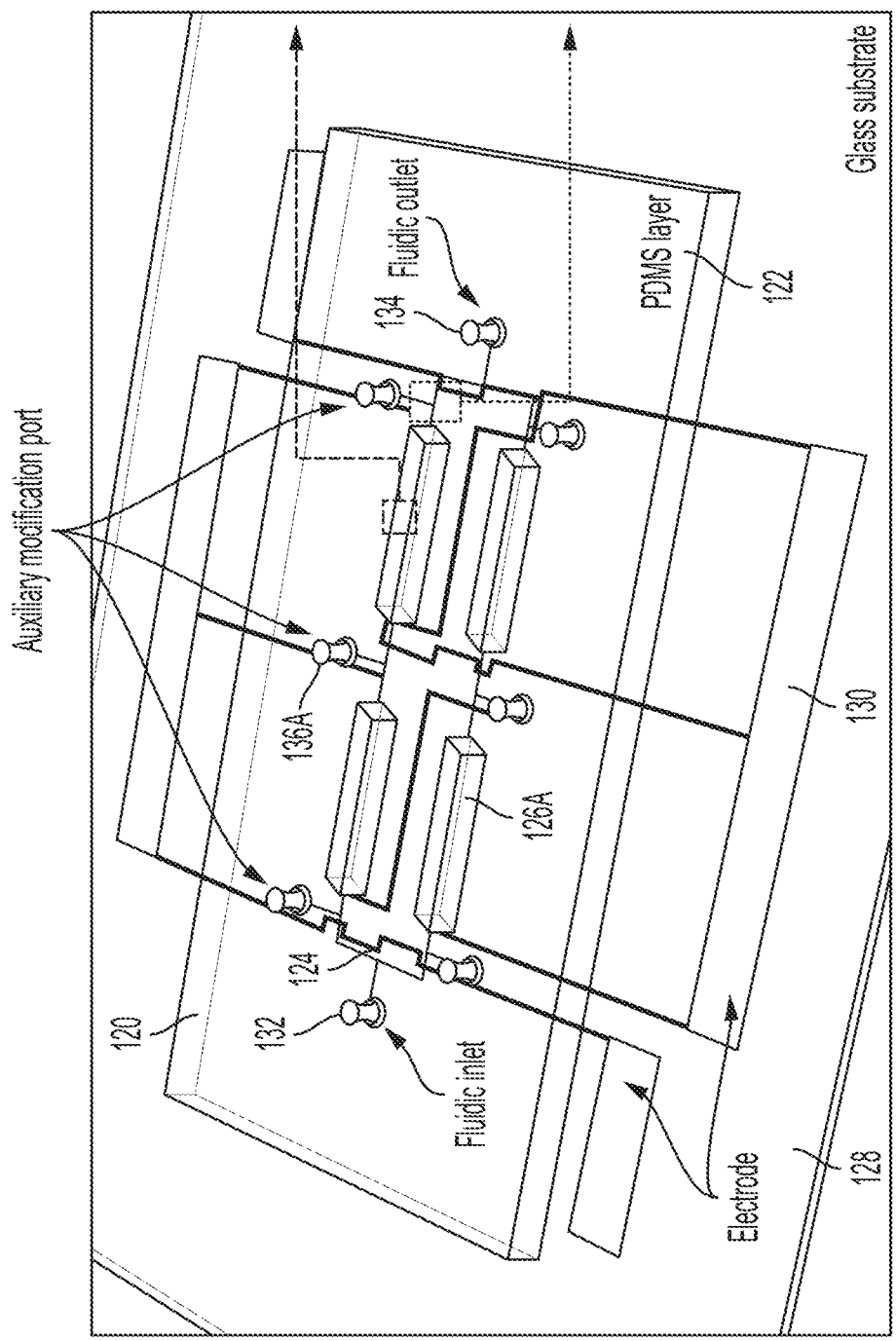

FIGS. 1a and 1b illustrate operational principle and design of an embodiment of an electronic antibody microarray. FIG. 1a is a schematic diagram showing the operation of the device. Each microfluidic cell capture chamber 102A-D is functionalized with a different antibody. Cells 104 expressing the target antigen are immunocaptured in the microfluidic chambers 102A-D. The number of captured cells in each chamber is determined by an on-chip network of electrical sensors 106A-F placed at strategic nodes across the device.

FIG. 1b shows a photo of the fabricated device 120 filled with blue dye for illustration. The fabricated device 120 is made up of a polydimethylsiloxane (PDMS) layer with microfluidic channels 124 and cell capture chambers, such as 126A, and a glass substrate 128 with a micropatterned metal layer 130 forming the sensor network. Besides the sample inlet 132 and outlet 134, auxiliary ports, such as 136A, were created on the microfluidic layer for selective functionalization of individual cell capture chambers.

Figure 1C:
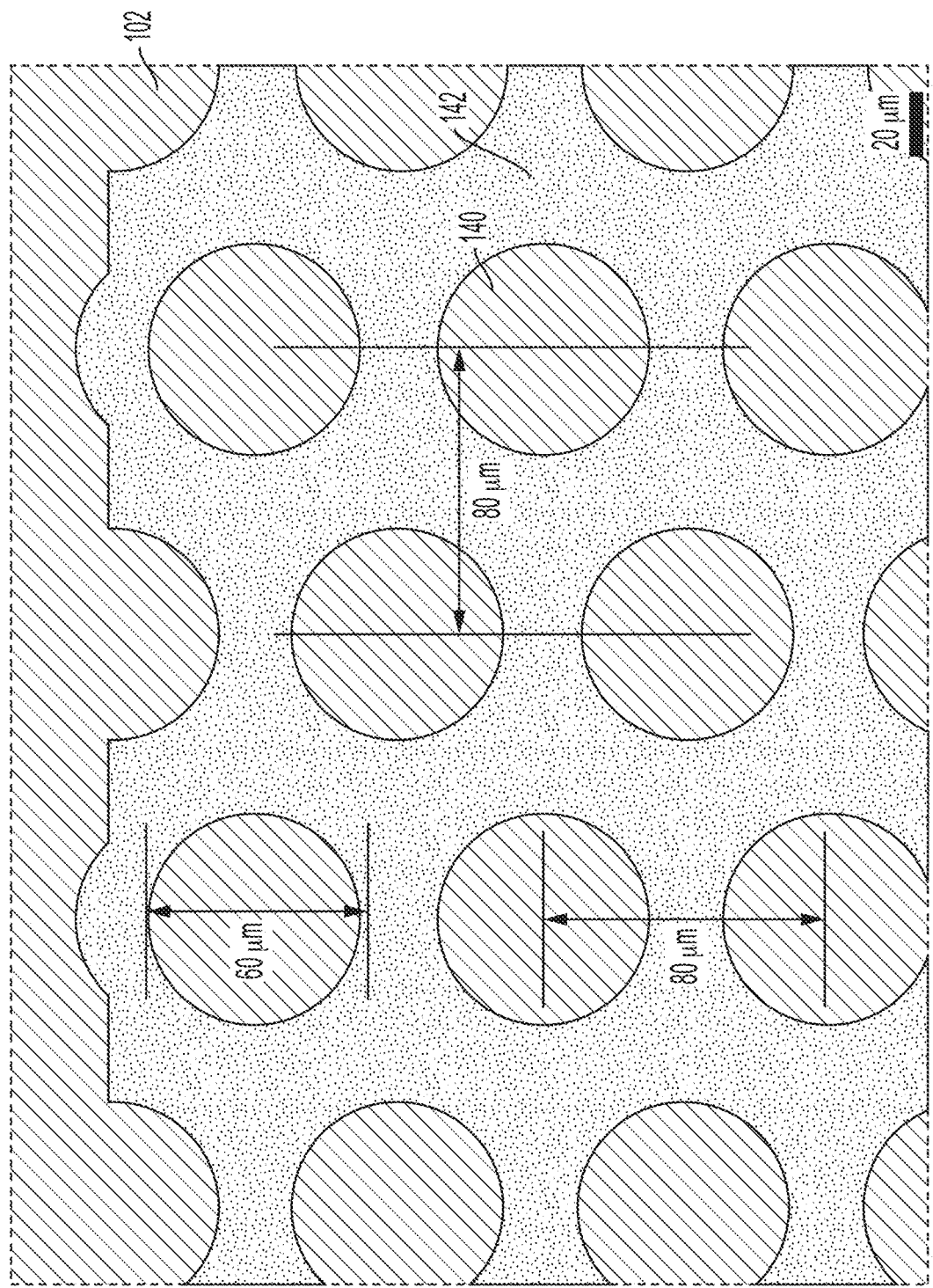
Figure 1D:
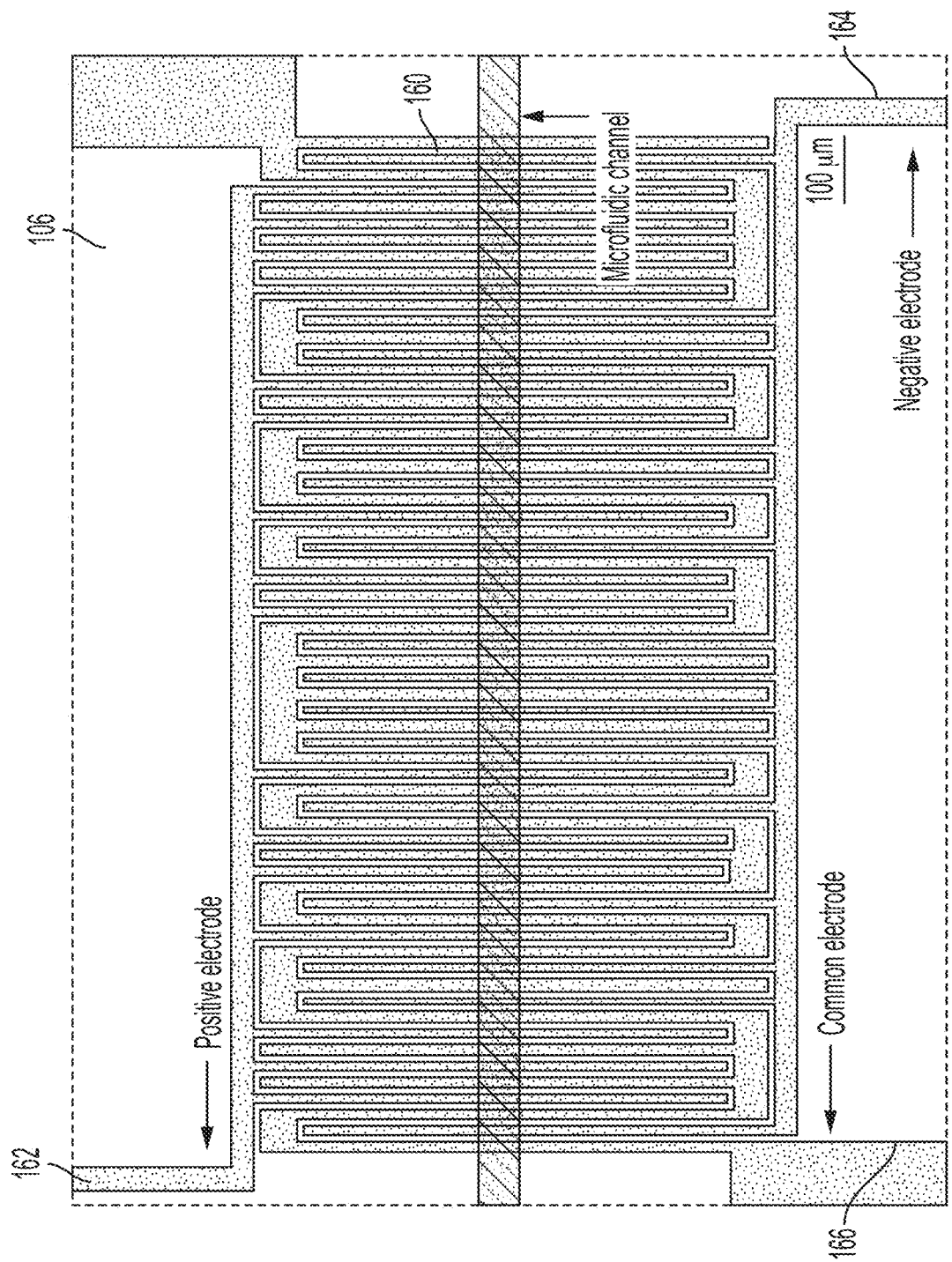

FIG. 1c shows a close-up image of the cell capture chamber 102. In embodiments, 60 μm diameter pillars 140, for example, may be arranged in a staggered array with an 80 μm pitch, for example, to enhance the cell capture rate. The channel 142 may be filled with a blue dye for visualization purposes in this image. FIG. 1d shows close-up image of one of the electrical sensors 106 on the device. The sensor may be specifically designed to form an electrode 160 pattern to produce a 31-bit digital code (in this example, 0111001011010000110100110011110), each time a cell flows over it. Other sensors may be coded with different orthogonal codes enabling a code-multiplexed readout shared by all sensors.

Device Design and Operation. Embodiments may be designed and fabricated in, for example, a two by two microfluidic antibody microarray with an electrical readout, as shown in FIG. 1b. Embodiments may be composed of a polydimethylsiloxane (PDMS) microfluidic layer that accommodates the cell capture chambers, as shown in FIG. 1c, and a glass substrate with a code-multiplexed Coulter sensor network made up of micropatterned gold electrodes, as shown in FIG. 1d. As shown, for example, in FIG. 1a, in the microfluidic layer, the sample inlet 108 may divide, for example, bifurcate 110 into two separate microfluidic paths 112A-B, with each path consisting of two cascaded cell capture chambers, such as 102A-B and 102C-D. In both microfluidic paths 112A-B, cells 104 may sequentially interact with two different antibodies immobilized in the microfluidic chambers 102A-D before all cells are merged 114 and discharged 116 from the waste outlet. In embodiments, code multiplexed Coulter sensors 106A-F may detect or log cells, such as each and every cell, as the cell enters the device if it passes from one capture chamber 102A-D to another, and if it gets discharged from the device, to determine the antigen-positive cell count in each cell capture chamber from a mass balance calculation.

In embodiments, microfluidic cell capture chambers may replace antibody spots in a conventional assay and may be designed to efficiently capture the cells expressing target surface antigens. For example, as shown in FIG. 1b, each cell capture chamber may measure 9 mm in length and 3 mm in width. Within each cell capture chamber, embodiments may include, for example, as shown in FIG. 1c, 60 μm diameter pillars 140 to increase the cell capture area and to structurally support the cell capture chamber ceiling. The pillars 140 may form a staggered 2D array with, for example an 80 μm pitch to increase the likelihood of cell-pillar contact under laminar flow. To selectively modify each chamber with a specific antibody, embodiments may include a set of auxiliary functionalization ports in the PDMS layer, such as port 136A, shown in FIG. 1b. These auxiliary ports may be located close to the inlet and outlet of each cell capture chamber, as shown in FIG. 1b, to exclusively deliver the functionalization reagents to the desired cell capture chamber. Following the functionalization process, the auxiliary ports may be sealed to prevent leakage during the assay, and the device was interfaced via a single fluidic inlet and outlet.

Figure 2A:
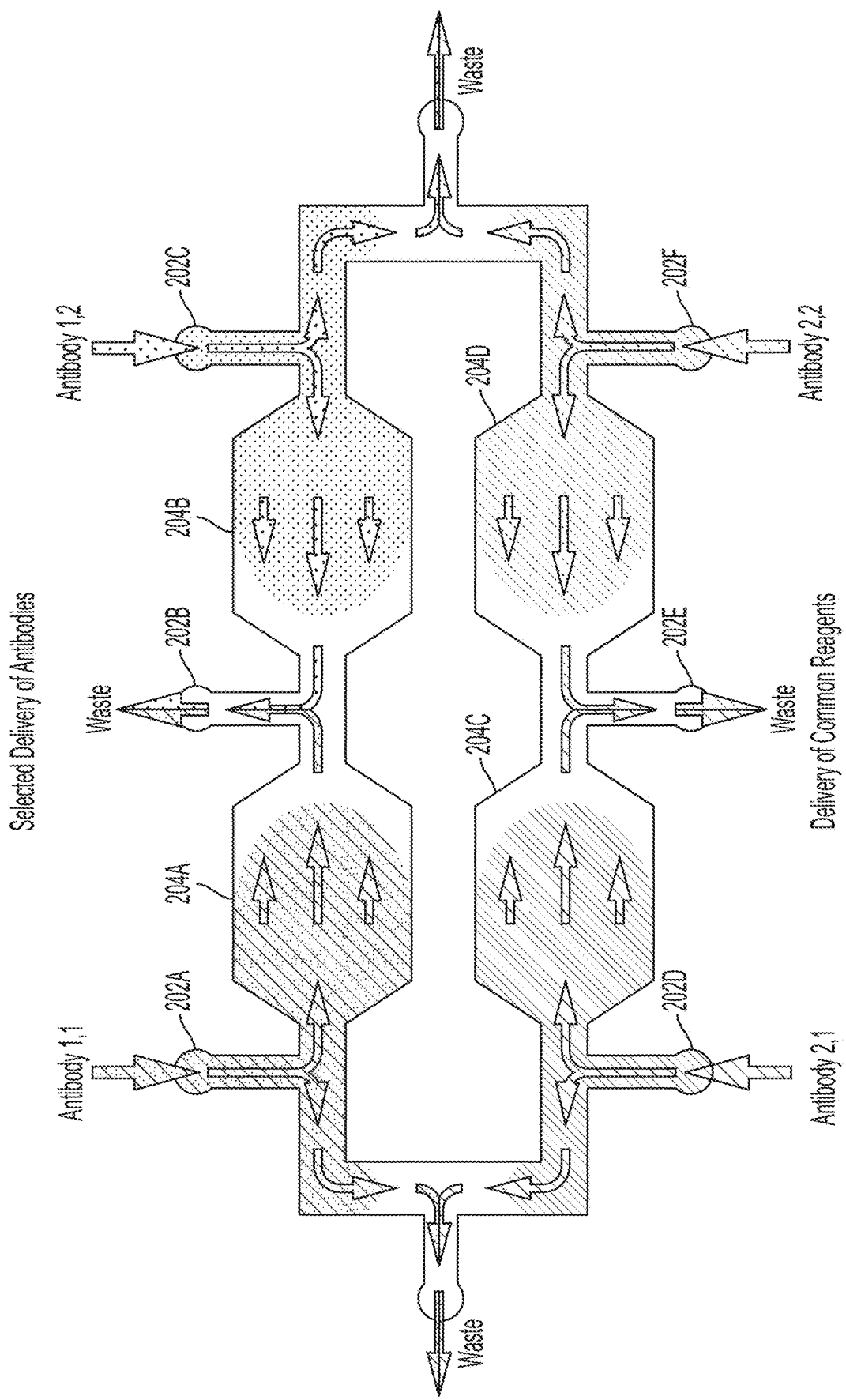
FIGS. 2a, 2b, 2c, and 2d illustrate an exemplary functionalization of cell capture chambers, according to embodiments of the present devices and methods.
Figure 2B:
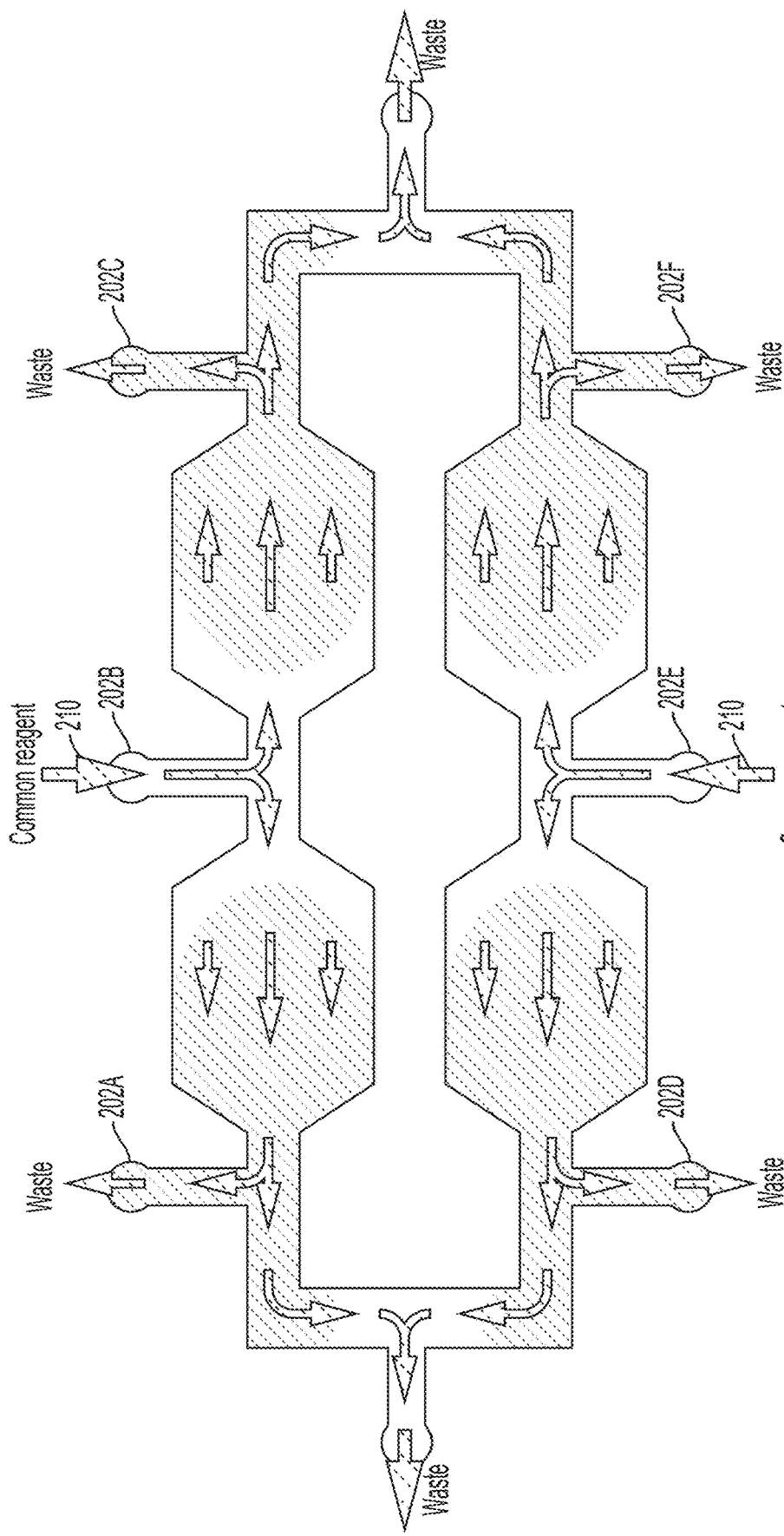
Figure 2C:
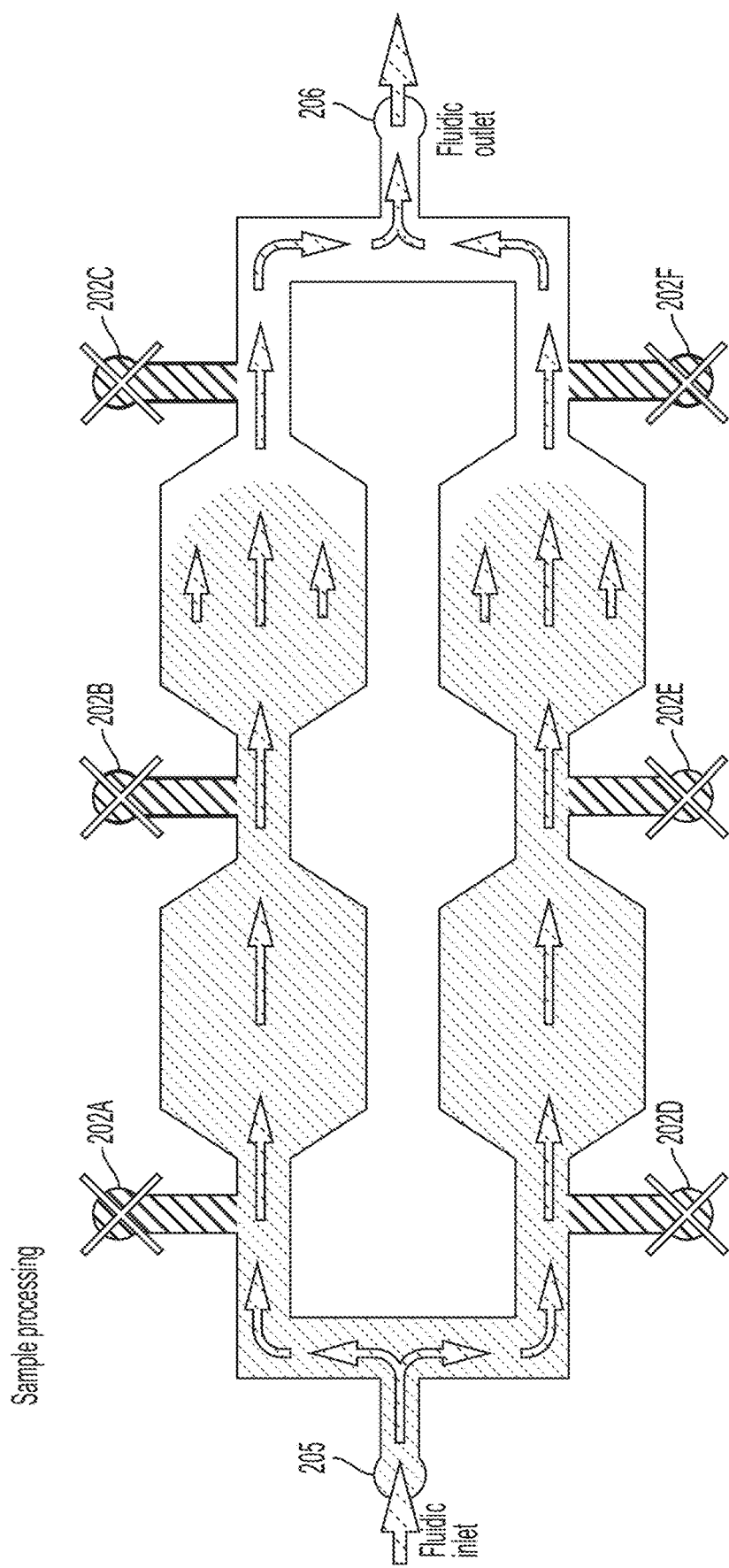
Figure 2D:
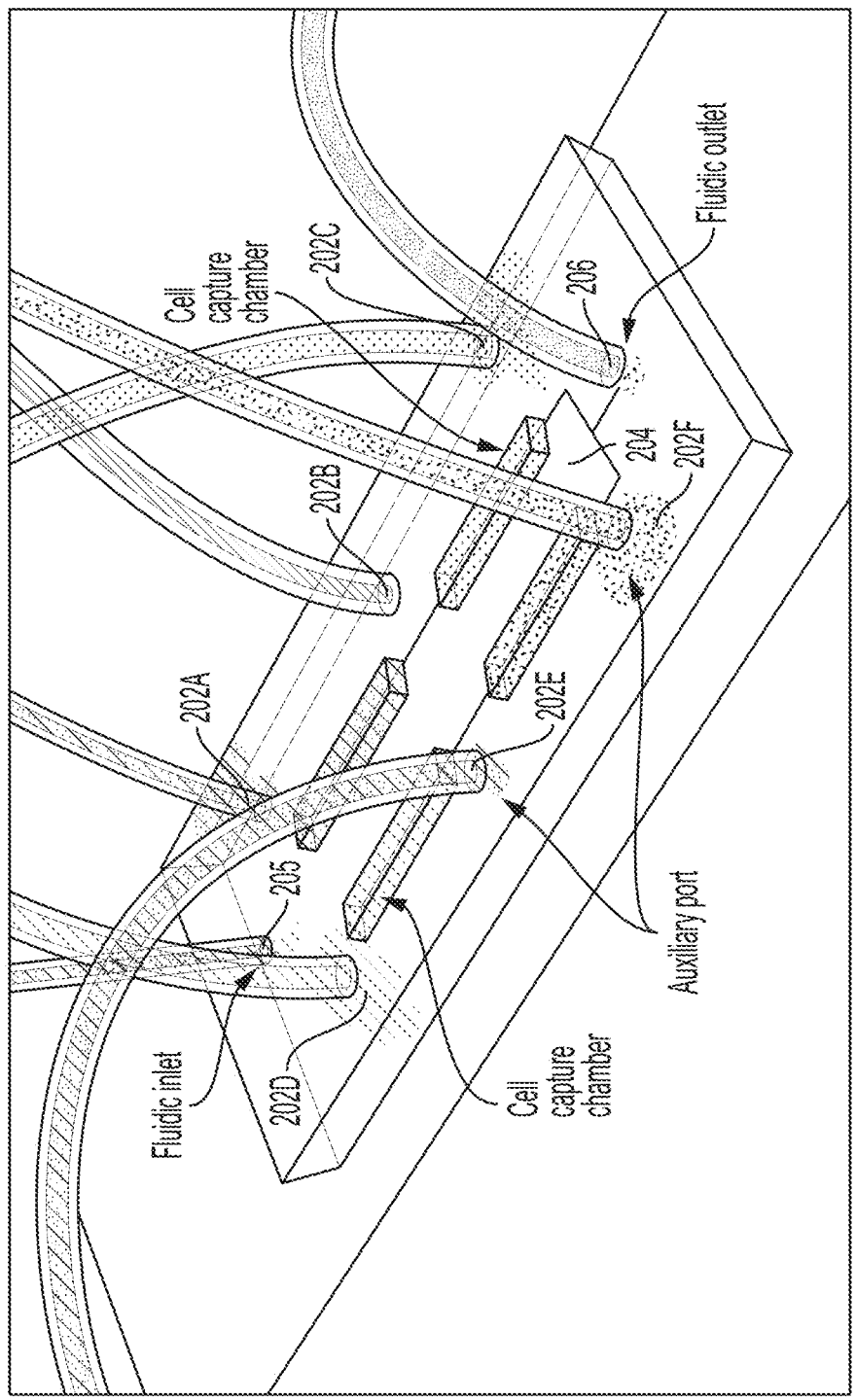

An example of functionalization of the cell capture chambers is shown in FIGS. 2a-2c. FIG. 2a depicts different schemes for interfacing the device for surface functionalization and sample processing. In this example, all four antibodies 1,1, 1,2, 2,1, and 2,2 may be simultaneously introduced from the auxiliary functionalization ports 202A-F to specifically and exclusively deliver the capture antibodies 1,1, 1,2, 2,1, and 2,2 to the desired cell capture chamber 204A-D. The laminar flow combined with the symmetric device design prevents any mixing between different antibody solutions. As shown in FIG. 2b, the buffers and reagents 210 common to all cell capture chambers may be introduced from an inlet 202B,E and the auxiliary functionalization ports 202A,C,D,F may operate as outlets. As shown in FIG. 2c, prior to sample processing, auxiliary functionalization ports 202A-F may be sealed. The sample may then be introduced from a single inlet 205 and the waste may be collected from a single outlet 206. FIG. 2d shows a photo of a device, where four different solutions each containing a different colored dye could successfully be delivered to individual cell capture chambers using the developed process. Lack of mixing between different colors demonstrates the capability to specifically deliver different antibodies to corresponding microfluidic chambers.

To functionalize cell capture chambers with antibodies, embodiments may employ a four-step chemical modification protocol (Immobilization of antibodies in the microfluidic device section as described below). To selectively immobilize different antibodies in the intended cell capture chambers, embodiments may use auxiliary functionalization ports, such as ports 202A-F, shown in FIG. 2a. In this process, capture antibodies for different cell capture chambers may be simultaneously introduced into the device through their dedicated functionalization ports 202A-F at the same flow rate, as shown in FIG. 2a. Simultaneous injection of antibody solutions 202A,C,D,F through symmetrically designed microfluidic paths combined with the laminarity of the flow ensured that each antibody is exclusively directed into the desired cell capture chamber without mixing with others. To minimize antibody loss from the waste ports 202B,E in this process, Tygon tubes may be employed to increase the hydraulic resistance of the waste path diverting most (≥80%) of the solution into the capture chambers. The characterization of this concurrent functionalization approach using different colored dyes demonstrated its effectiveness with no observable crosstalk between different cell capture chambers, as shown in FIG. 2b. While the diffusion across different cell capture chambers during incubation may induce mixing, the distance between different chambers makes its effect negligible in the functionalization of cell capture chambers. Embodiments may provide advantages over the printing-based deposition of antibodies, such as: First, we can perform the whole functionalization process in a closed chamber without exposing the antibodies to the ambient during buffer exchanges. Second, we functionalize all inner surfaces of the microfluidic chambers, which enhances capture efficiency. It should also be noted that except for the antibodies, auxiliary functionalization ports were used as outlets in the functionalization process for applying reagents common to all cell capture chambers, such as (3-aminopropyl)triethoxysilane (APTES) and glutaraldehyde, as may be used as shown in FIG. 2b. Once the functionalization process is completed, all auxiliary functionalization ports 202A-F may be sealed, and the sample may be introduced to the device from a common inlet 205, and the waste may be discharged from the common outlet 206, as shown in FIG. 2c. Overall, the functionalization process utilizes the same chemistry employed for preparing immunoassays and can also be scaled to create larger assays with more antibodies.

To electrically measure the number of captured cells in each of the functionalized cell capture chambers, embodiments may employ a network of coded Coulter sensors 106A-F, shown in FIG. 1a, distributed across the device. A sensing strategy may be based on the Microfluidic coded orthogonal detection by electrical sensing (CODES) scheme, which uses micromachined electrode patterns to multiplex spatiotemporal cell data across a microfluidic device. In an embodiment, a three-electrode Coulter counter may be shaped to form distinct electrode patterns (i.e., sensors) at six different nodes to monitor cell passage between microfluidic chambers. Each sensor may be composed of an array of 5 µm wide finger electrodes separated by 5 µm gaps and may produce a specific 31-bit digital code, which may be implemented by an interdigitated arrangement of three electrodes: two sensing electrodes to set the bit polarity (positive 162 for "1" and negative 164 for "0") and one common electrode 166 meandering in between to excite the sensor network, as shown in FIG. 1d. Cells flowing over one of these sensors may sequentially modulate the local impedance between adjacent finger electrodes via the Coulter principle and generated a distinct bipolar electrical waveform dictated by the surface electrode pattern. In addition, embodiments may use sensor codes designed to be mutually orthogonal (Gold sequences), and therefore, embodiments may 1) reliably discriminate sensor signals from each other in the output signal and 2) resolve interfering signals when multiple cells are coincidentally detected by the same or different sensors, for example, as shown in Table 1. Moreover, in the case of cell debris or aggregates, the electrical signal generated by sensors do not match any of the templates constructed based on single cell signals and therefore, these data are discarded and do not affect the assay performance.

Examples of Gold codes used in the multiplexed sensor network for the antibody microarray and the individual cell count from each coded Coulter sensor are shown in Table 1.

| Coded sensor | Code | Cell count |
|---|---|---|
| Code 1, 1 | 1010111011000111110011010010000 | $c_{11}$ |
| Code 1, 2 | 0001101111011010001111110100000 | $c_{12}$ |
| Code 1, 3 | 0111001011010000101001100111110 | $c_{13}$ |

-continued

| Coded sensor | Code | Cell count |
|---|---|---|
| Code 2, 1 | 1011010100011101111100100110000 | $c_{21}$ |
| Code 2, 2 | 0100110010111001110110011101000 | $c_{22}$ |
| Code 2, 3 | 1001010001000000011111011111101 | $c_{23}$ |

Figure 3:
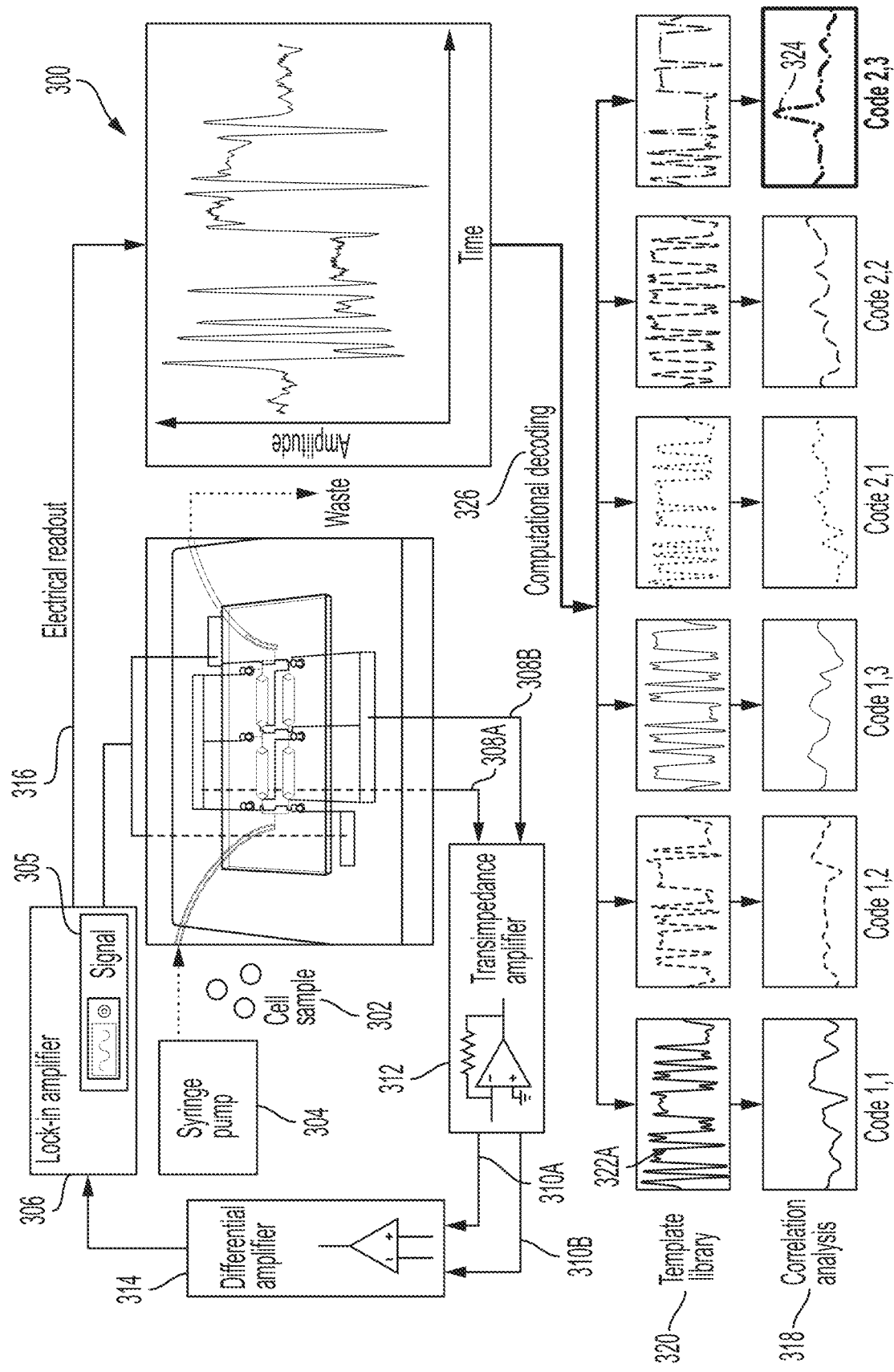
FIG. 3 illustrates an example of electrical acquisition of cell capture statistics across the antibody microarray, according to embodiments of the present devices and methods.

An example of the electrical acquisition of the cell capture statistics across the antibody microarray is shown in FIG. 3. An exemplary schematic diagram of an experimental setup 300 used for the sample delivery and electrical measurements. Cells 302 may be driven through the device at a constant flow rate with a syringe pump 304. An electrical sensor network 106A-F, shown in FIG. 1a, may excited using a sine wave 305 generated from the lock-in amplifier 306, and the resulting current signals 308A-B may be first converted to voltage signals 310A-B using transimpedance amplifiers 312, then subtracted from each other by a differential amplifier 314 and the signal amplitude 316 is measured using a lock-in amplifier 306. The decoding process may then identify individual sensor signals in the device output signal 316. The output signal 316 may be correlated 318 with a template library 320 consisting of signature waveforms, such as 322A, corresponding to each and every coded sensor in the network using a custom-built algorithm 318. A correlation peak 324 may be used to identify the matching template and the specific sensor that detected the cell. The specific case in the figure demonstrates the decoding of a signal produced by the sensor with the Code 2,3.

During an exemplary assay, the sample was driven through the functionalized device by a syringe pump 304 at a controlled flow rate and followed by a brief phosphate buffered saline (PBS) wash to clear the device of remaining cells. The electrical signal 316 from the device was acquired via electronic hardware and analyzed using a computer 326, as described below. To determine a capture location for each cell processed on the device, we processed the output signal 316 using a custom-built decoding algorithm 318. In this example, the algorithm was implemented in the LabVIEW (National Instruments) and processed the data with minimal manual intervention. Briefly, our algorithm first reviewed a part of the recorded electrical waveform, identified different code signals present, and classified them into different sensor groups. Once each sensor group contains a sufficient number of code signal instances, signals were normalized and averaged to form a library of code templates that correspond to each and every sensor in the network. The generation of templates based on recorded signals from the sample itself made the templates specific to both the sample and the device, thereby increasing accuracy. The templates were then used to process all sensor data by correlating the output signal with the template library. Because the code signals were specifically designed to be mutually orthogonal, we could not only classify sensor signals robustly with minimal crosstalk but also resolve signal interferences through an iterative process called successive interference cancellation. At the end of this decoding process, the original output waveform was decomposed into data from individual sensors, which was then used to calculate cell capture statistics across the whole device. Specifically, the number of captured cells in each chamber was obtained, by subtracting the exit node cell count from the entry node cell count (Table 1 and Table 2).

The calculation of the fraction of cells captured in each chamber and noncaptured cells discharged into the waste from electrical data is shown in Table 2:

| Chamber | Immunophenotype | Fraction |
| --- | --- | --- |
| Chamber 1, 1 | EpCAM$^{pos}$ | $p_{11} = (c_{11} - c_{12})/c_{11}$ |
| Chamber 1, 2 | EpCAM$^{neg}$CD49f$^{pos}$ | $p_{12} = (c_{12} - c_{13})/c_{11}$ |
| Outlet 1 | EpCAM$^{neg}$CD49f$^{neg}$ | $p_{1end} = c_{13}/c_{11}$ |
| Chamber 2, 1 | CD49f$^{pos}$ | $p_{21} = (c_{21} - c_{22})/c_{21}$ |
| Chamber 2, 2 | CD49P$^{neg}$EpCAM$^{pos}$ | $p_{22} = (c_{22} - c_{23})/c_{21}$ |
| Outlet 2 | CD49P$^{neg}$EpCAM$^{neg}$ | $p_{2end} = c_{23}/c_{21}$ |

Figure 4A:
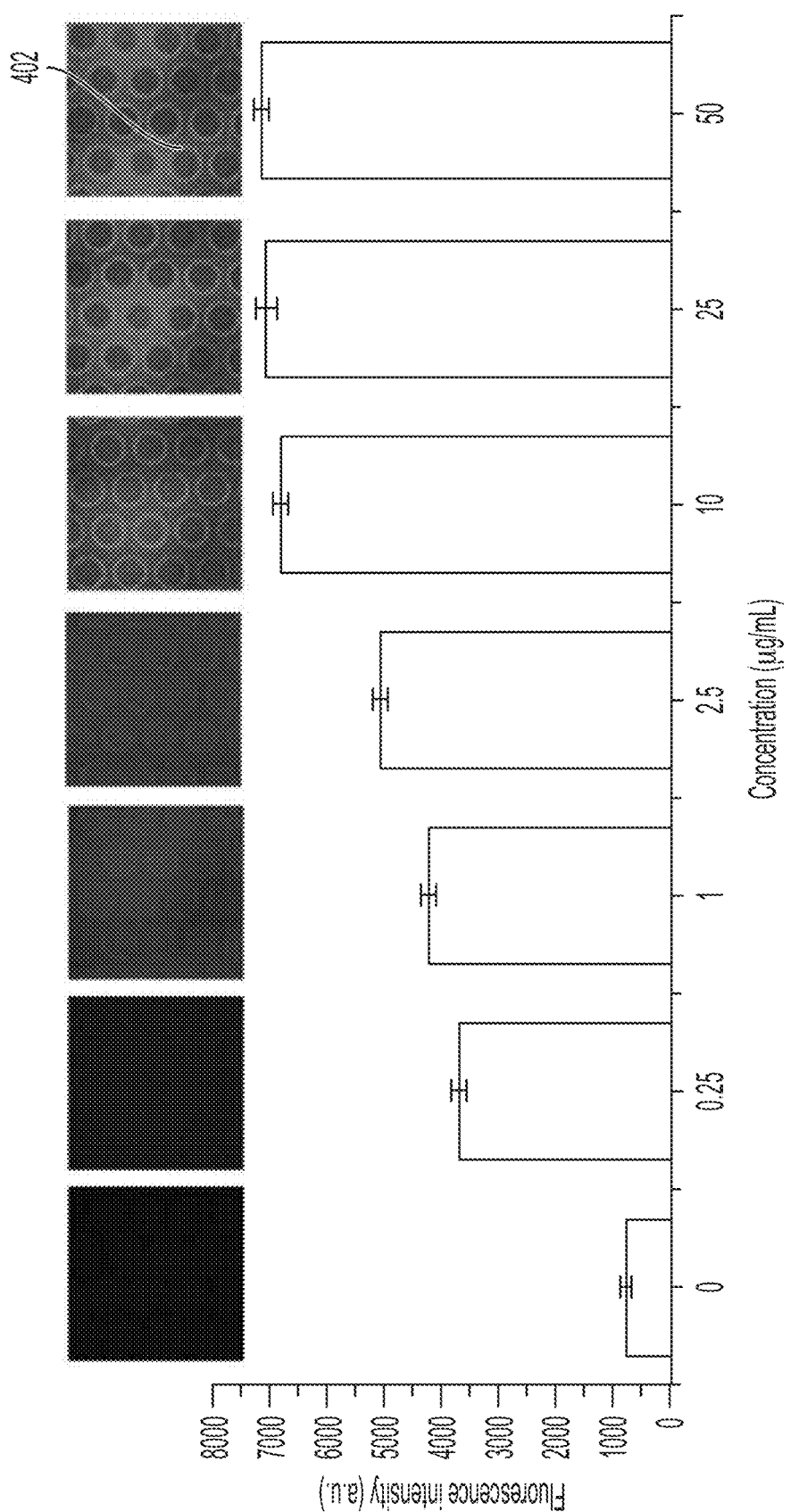
FIGS. 4a, 4b, 4c, 4d, and 4e illustrate an example of optimization of the surface chemistry and processing conditions for efficient cell capture in microfluidic chambers, according to embodiments of the present devices and methods.
Figure 4B:
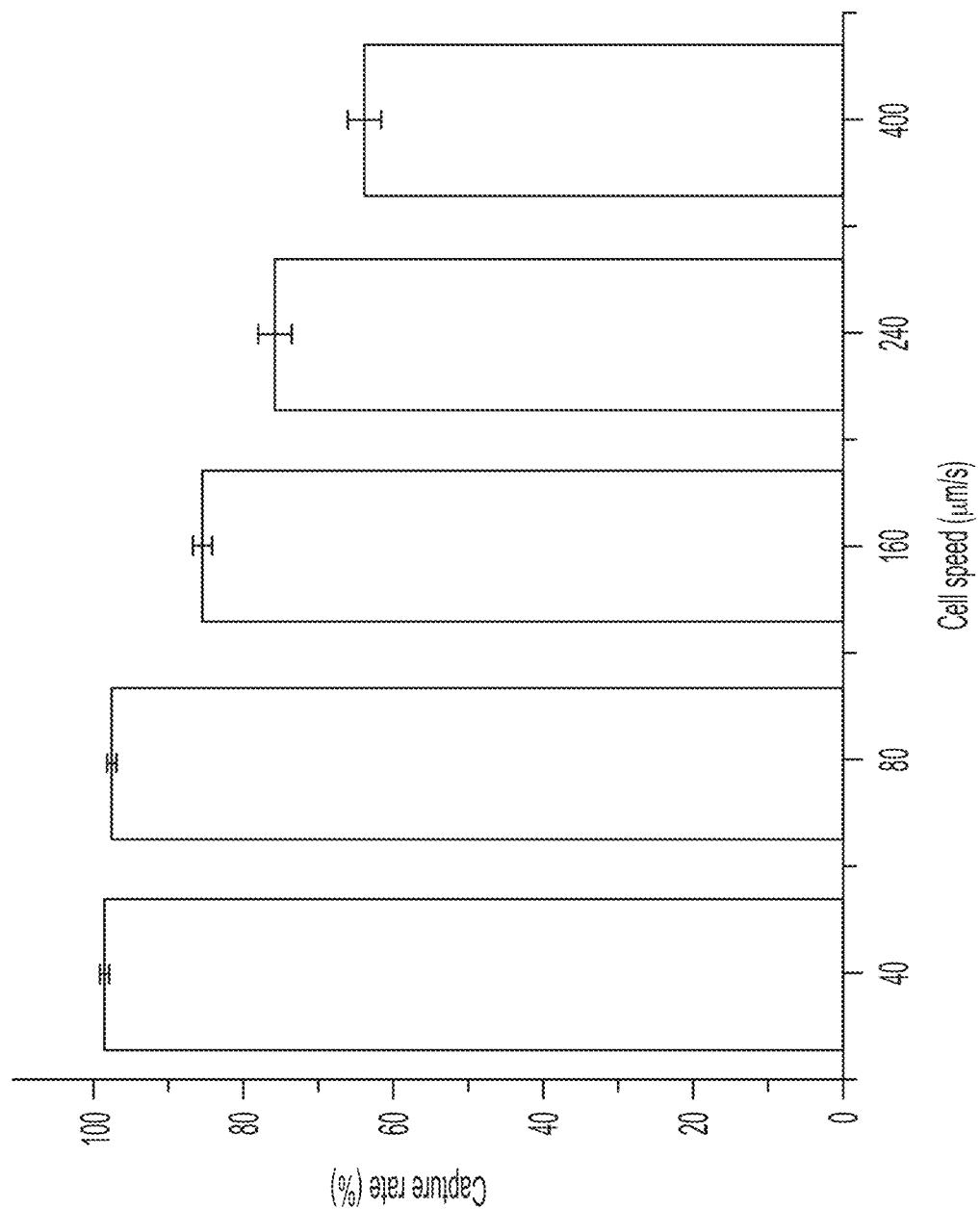
Figure 4C:
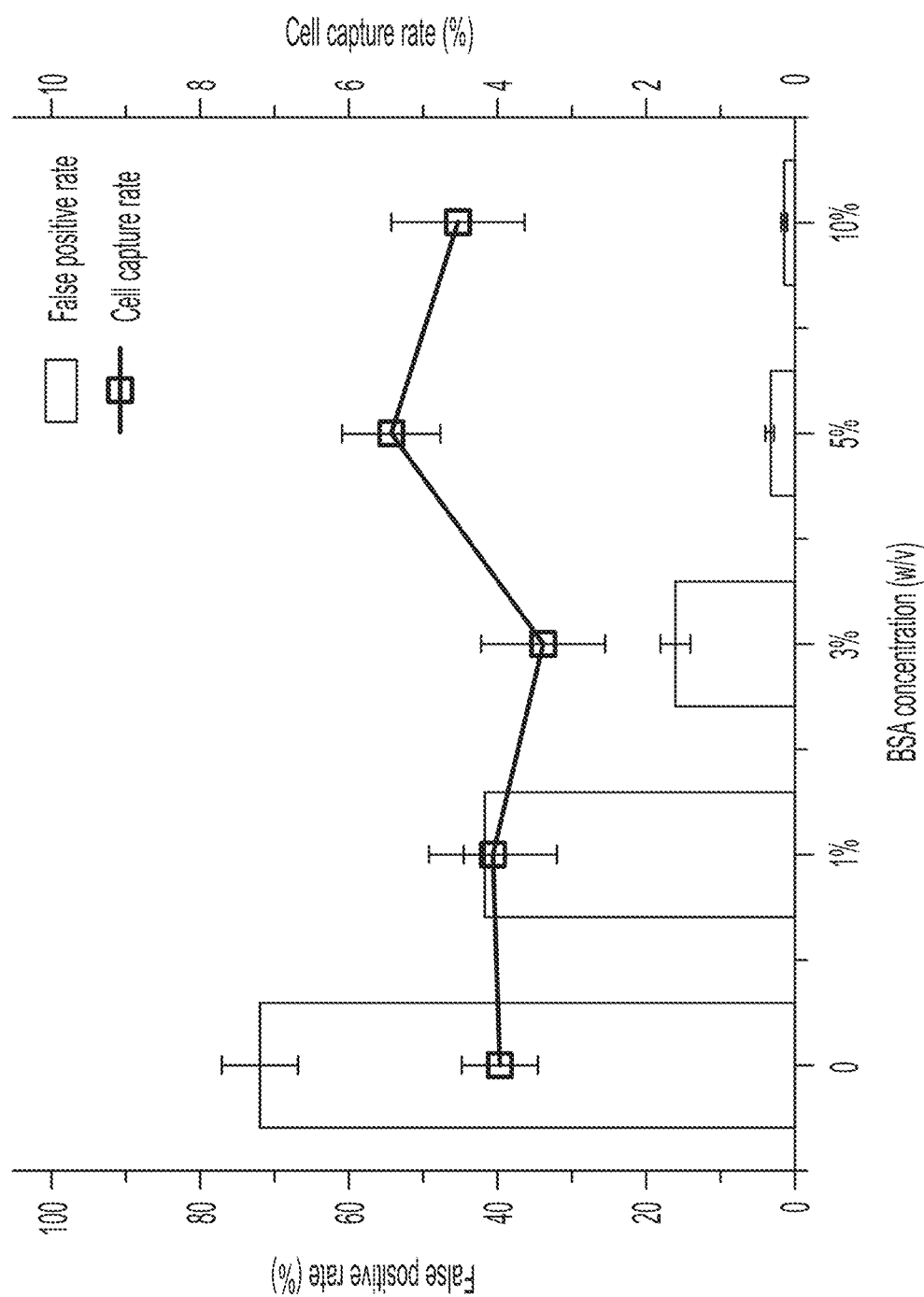
Figure 4D:
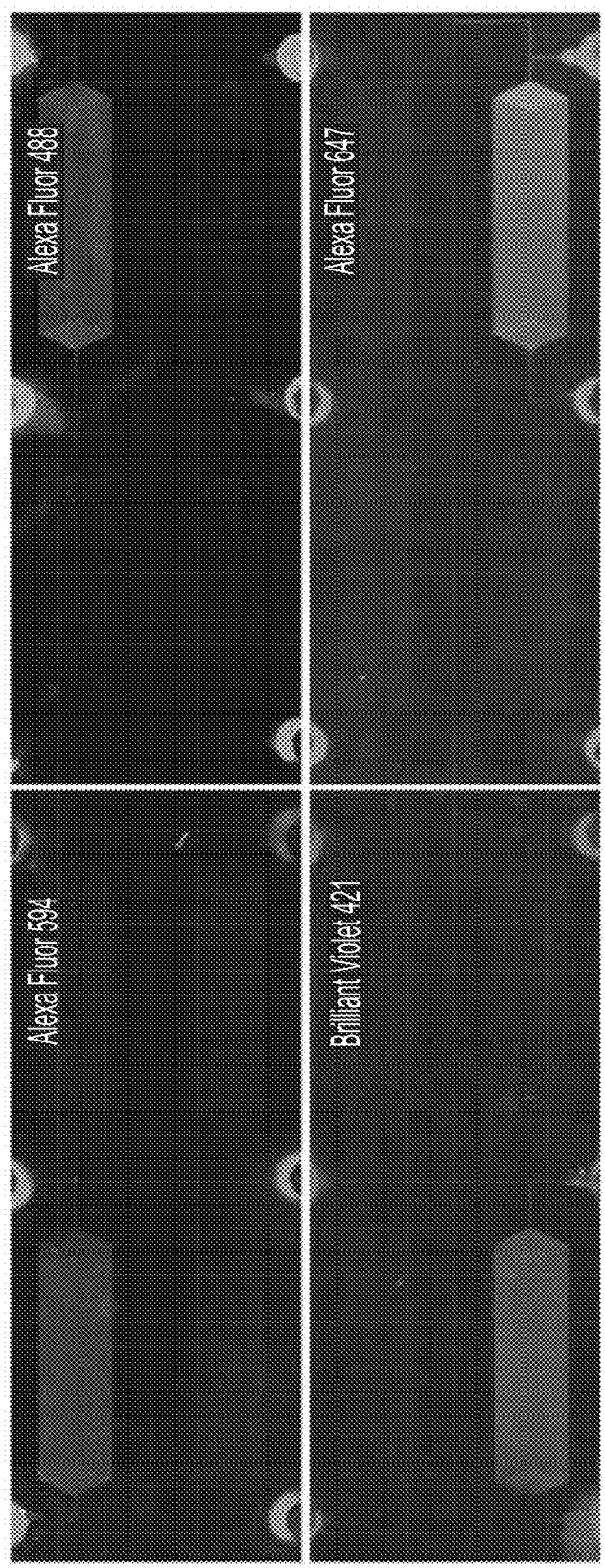
Figure 4E:
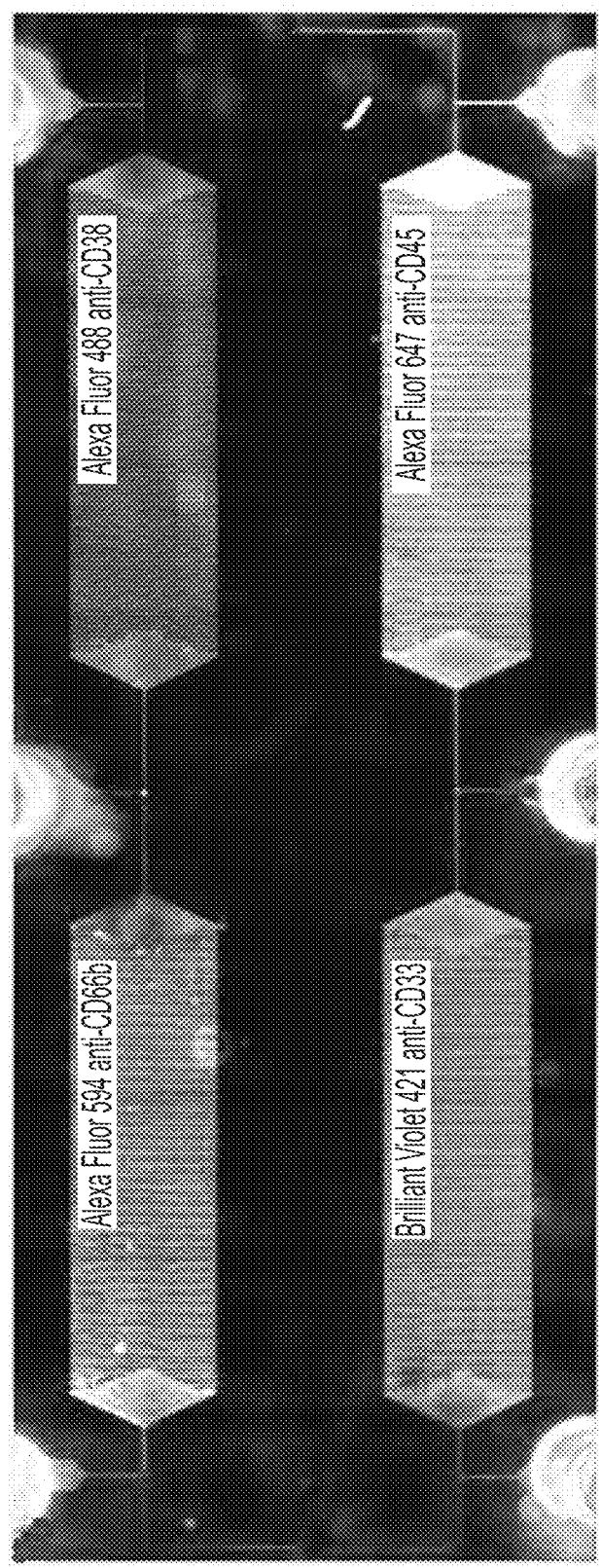

FIGS. 4a-e show examples of optimization of the surface chemistry and processing conditions for efficient cell capture in microfluidic chambers. FIG. 4a shows an example of optimization of the capture antibody amount immobilized on the device surface. Devices were functionalized with FITC-conjugated anti-CD45 antibody at concentrations ranging from 0 to 50 µg mL$^{-1}$. The amount of the immobilized antibody at different concentrations was measured from the fluorescence intensity. FIG. 4b shows an example of optimization of the sample flow speed. Measured leukocyte capture rates in devices functionalized with anti-CD45 as a function of sample flow rates ranging from 40 to 400 µm s$^{-1}$. FIG. 4c shows an example of optimization of the BSA concentration for minimizing nonspecific cell capture. Nonspecific cell capture rate was measured at BSA concentrations ranging from 0% to 10%. FIG. 4d shows an example of optimization of specific functionalization of microfluidic chambers with four different capture antibodies. In this example, single-channel fluorescence images show the exclusive immobilization of capture antibodies, each labeled with a different fluorophore, in the corresponding cell capture chambers. Each capture chamber is uniformly coated, and no crosstalk can be observed between cell capture chambers. FIG. 4e shows an example of optimization of specific functionalization of microfluidic chambers with four different capture antibodies. In this example, four-channel fluorescence image of the whole device shows the successful functionalization of cell capture chambers. The boundaries between different antibodies are visible along the microfluidic channels that connect cell capture chambers. (Error bars represent standard deviation.)

Optimization of the Cell Capture Parameters. Cells expressing the target antigens and yet not captured by our device lead to false negative results. Therefore, to maximize cell capture efficiency, we first optimized the amount of antibody to coat the microfluidic cell capture chambers. To measure the antibody coverage on the surface, we employed fluorophore-conjugated antibodies and imaged the functionalized device with fluorescence microscopy. Cell capture chambers were first functionalized with fluorescein isothiocyanate (FITC) anti-CD45 antibody at concentrations ranging from 0.25 µg mL$^{-1}$ to 50 µg mL$^{-1}$ using the immobilization protocol (Immobilization of antibodies in the microfluidic device in the Experimental Section). We observed higher fluorescence emission with increasing antibody concentration, and the differential emission between antibody concentrations was especially apparent on micropillar surfaces, where deposited fluorophoreconjugated antibody formed high contrast annular patterns around the cross-sections of the pillars, as shown in FIG. 4a, for example at 402. Quantitative measurements of mean fluorescence intensities for different concentrations showed a drastic increase in surface antibody concentration until 10 µg mL$^{-1}$ and the changes in fluorescence beyond 25 µg mL$^{-1}$ were not notable, indicating surface saturation as shown in FIG. 4a. Based on these results, we selected 25 µg mL$^{-1}$ as the optimum incubation concentration to ensure complete coverage of the device surface with capture antibodies.

We also investigated the sample flow speed as a parameter to optimize the cell capture rate in our microfluidic device. The flow speed is an important factor in our assay because the cell immunocapture is a process with a binary outcome that depends on both the number of matching antibody-antigen pairs and the antibody-antigen interaction time, controlled by the sample flow speed. To optimize sample flow speed, we first functionalized the cell capture chambers with anti-CD45 antibody and tested the leukocyte capture performance under different flow rates. To quantify the effect of sample flow speed on the capture rate, we drove leukocytes through the microfluidic device at flow speeds ranging from 40 to 400 µm s$^{-1}$ using a syringe pump and measured the fraction of captured cells in the microfluidic chamber. As anticipated, the cell capture rate showed a strong dependence on the flow speed decreasing from ≈99% for flow rates 80 µm s$^{-1}$ to ≈64% at 400 µm s$^{-1}$, as shown in FIG. 4b. Based on minimal observed differences between cell capture rates below 80 µm s$^{-1}$ and considering potential problems at low flow rates such as sedimentation and nonspecific adhesion induced artifacts, we chose 80 µm s$^{-1}$ as the optimal sample flow speed for our assay. Similar optimization experiments have also been performed for the other antibodies used in this work, and we found that at 80 µm s$^{-1}$, all produced ≥96% capture rates. It should also be noted that the sample flow speed could be used as a physical gating mechanism since the required number of the antibody-antigen pairs in the cell adhesion process is related to the interface contact time. For example, a higher cell velocity would increase the minimum number of the antibody-antigen pairs required for cell capture, which would be analogous to a lower gate size in the post analysis of flow cytometry data. Likewise, a lower flow velocity can be used to compensate for a low affinity antibody-antigen pair and enhance the assay sensitivity.

To ensure specific capture of target cells in microfluidic capture chambers, we minimized nonspecific cell adhesion by blocking the functionalized device surface with bovine serum albumin (BSA). To determine the optimum BSA amount, we first functionalized devices at the predetermined optimum antibody concentration (25 µg mL$^{-1}$) and treated them with BSA solutions with concentrations ranging from 0% to 10% w/v for 1 h. After washing the devices with PBS, we drove leukocytes at the optimum flow speed (80 µm s$^{-1}$) and measured the nonspecific cell capture rate. In these measurements, we specifically chose the anti-CD115 as the capture antibody since the CD115 is expressed only by <10% of leukocytes (i.e., some monocytes), making most leukocytes potential targets for the nonspecific capture. To distinguish specific monocyte capture from nonspecific cell capture, captured leukocytes were post labeled with Alexa Fluor 488 anti-CD115 and counted with fluorescence microscopy. With increasing BSA concentration, nonspecific cell capture rate decreased from >70% for nonblocked devices to ≈2% for devices treated with a 10% BSA solution, as shown in FIG. 4c. Finally, we confirmed that specific cell capture was not confounded by blocking, because the capture rate of CD115$^{pos}$ leukocytes remained virtually constant across different BSA concentrations (FIG. 4c, red line). Based on these results, we selected the 10% BSA solution as the optimal blocking buffer for our assay. Following the optimization of surface chemistry for efficient and specific cell capture, we investigated the selective immobilization of capture antibodies to designated cell capture chambers. Specifically, we attempted to coat each of the four cell capture chambers with a different antibody via auxiliary functionalization ports based on the protocol described previously and inspected the resultant spatial arrangement of antibodies across the device with microscopy. To distinguish between different antibodies on the device, we specifically used antibodies conjugated with different-colored fluorophores (Alexa Fluor 594, Alexa Fluor 488, Brilliant Violet 421, and Alexa Fluor 647). Fluorescence images of the functionalized device showed that 1) each cell capture chamber was exclusively coated with the intended capture antibody, as shown in FIG. 4d, 2) there was no crosstalk between the different chambers as evidenced by distinct boundaries between different immobilized antibodies in the microfluidic channels that connect cell capture chambers, as shown in FIG. 4e, and 3) the antibody coverage was uniform throughout all cell capture chambers. It should also be noted that antibodies immobilized external to the cell capture chambers do not constitute a problem for our assay since 1) cells flow much faster (40×) in microfluidic channels preventing them to be captured on electrodes and 2) any cell trapped at the inlet or outlet reservoirs due to slower flow remain outside of the electrical detection nodes and therefore are not counted.

Figure 5A:
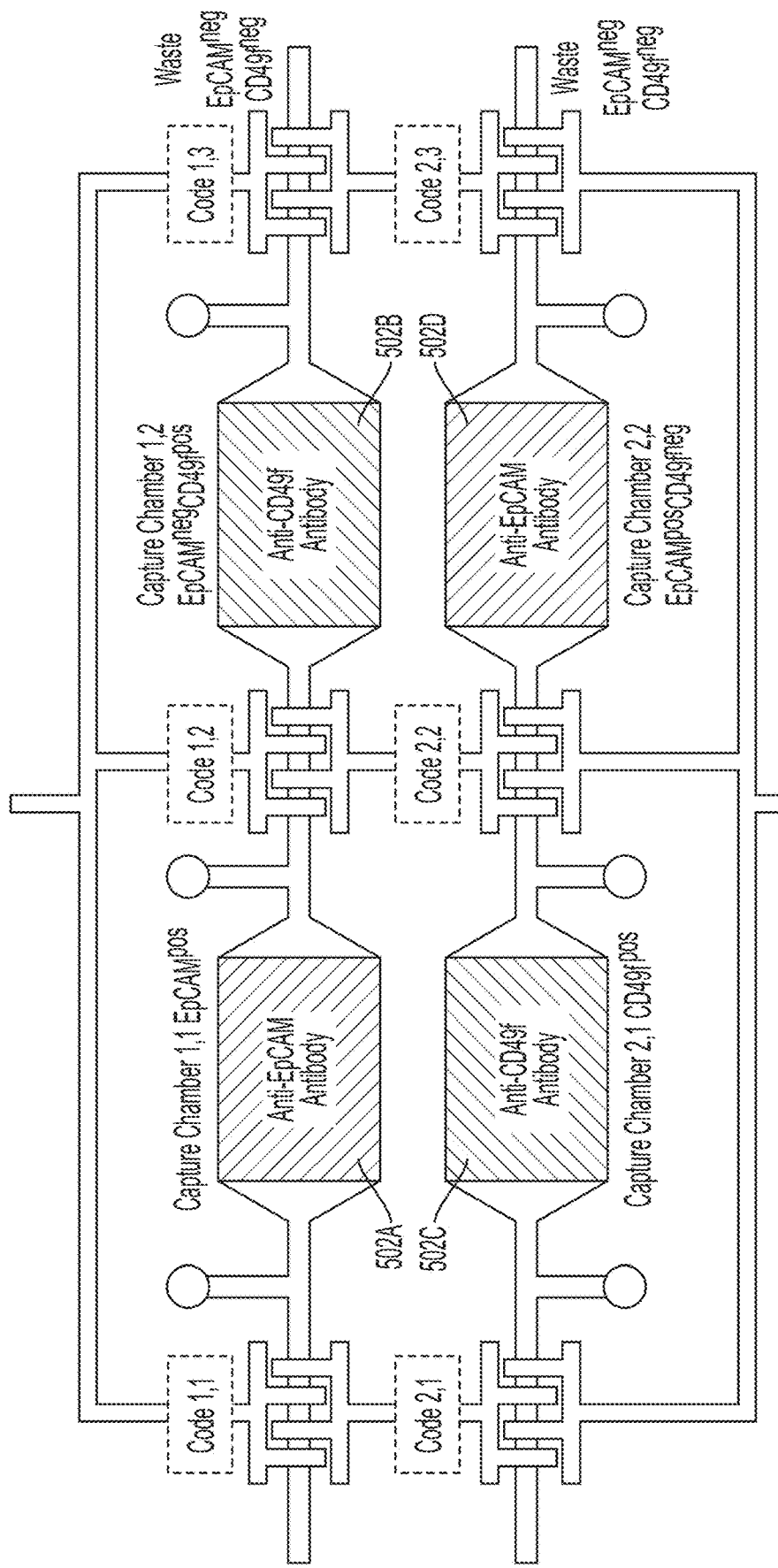
FIGS. 5a, 5b, 5c, 5d, 5e, 5f, 5g, and 5h illustrate an example of immunophenotyping of tumor cell mixtures, according to embodiments of the present devices and methods.
Figure 5B:
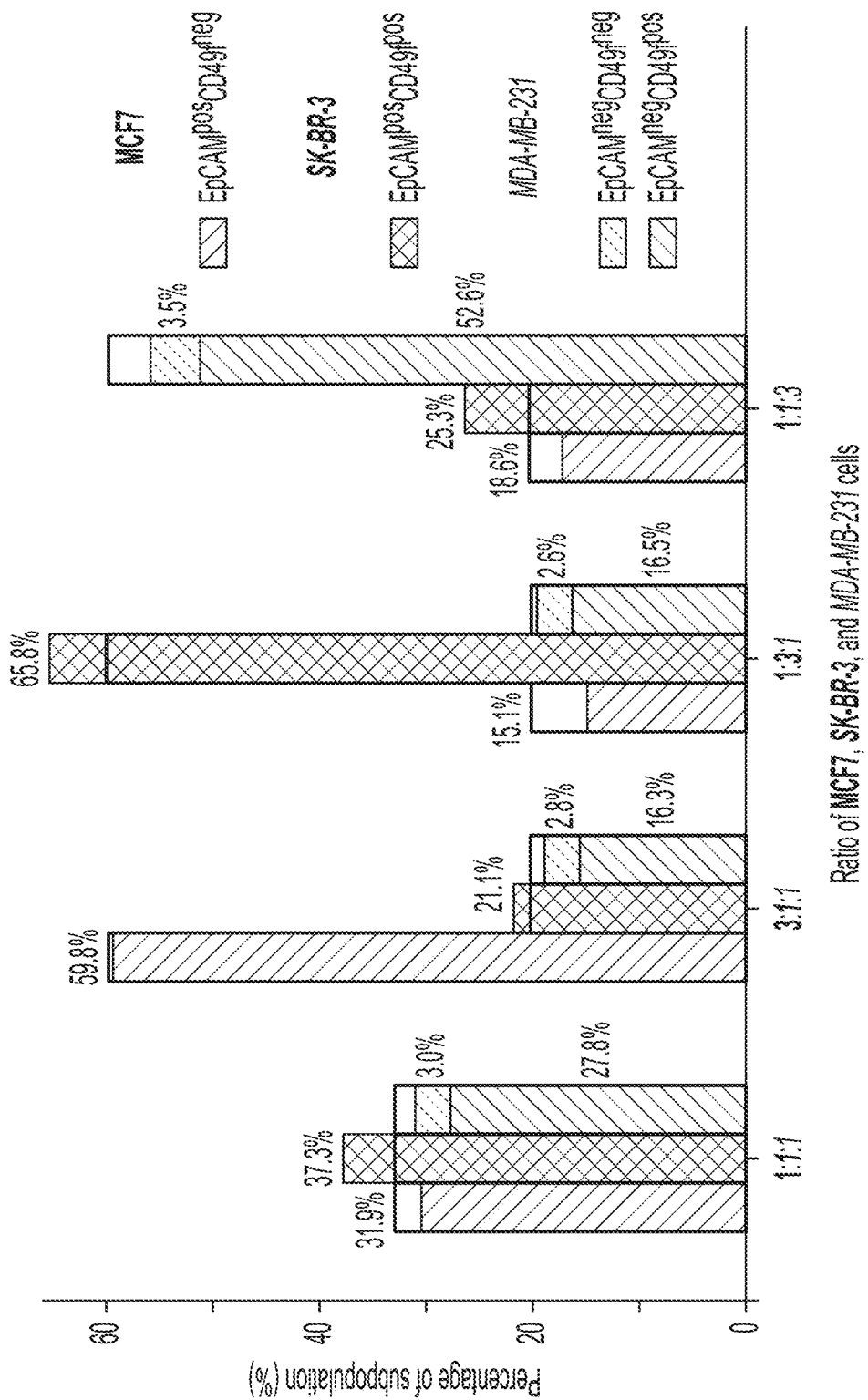
Figure 5C:
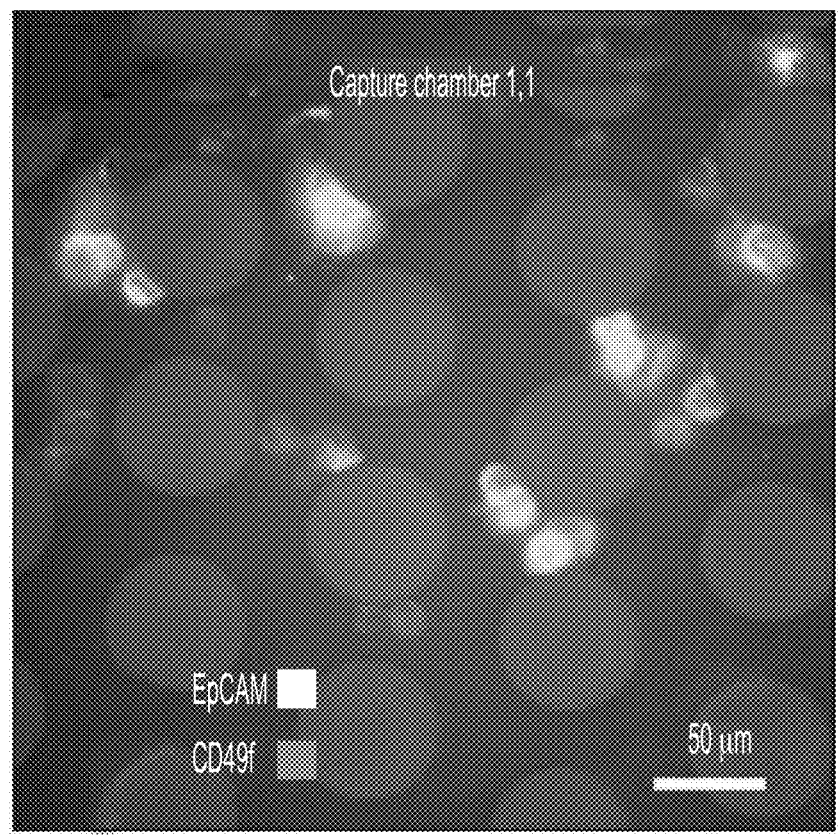
Figure 5D:
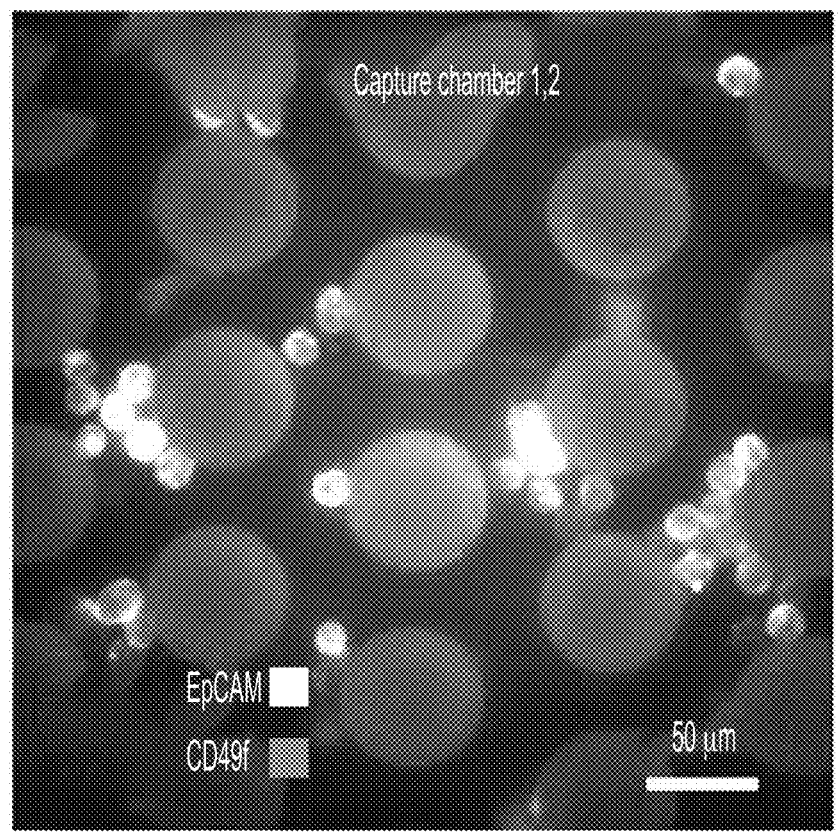
Figure 5E:
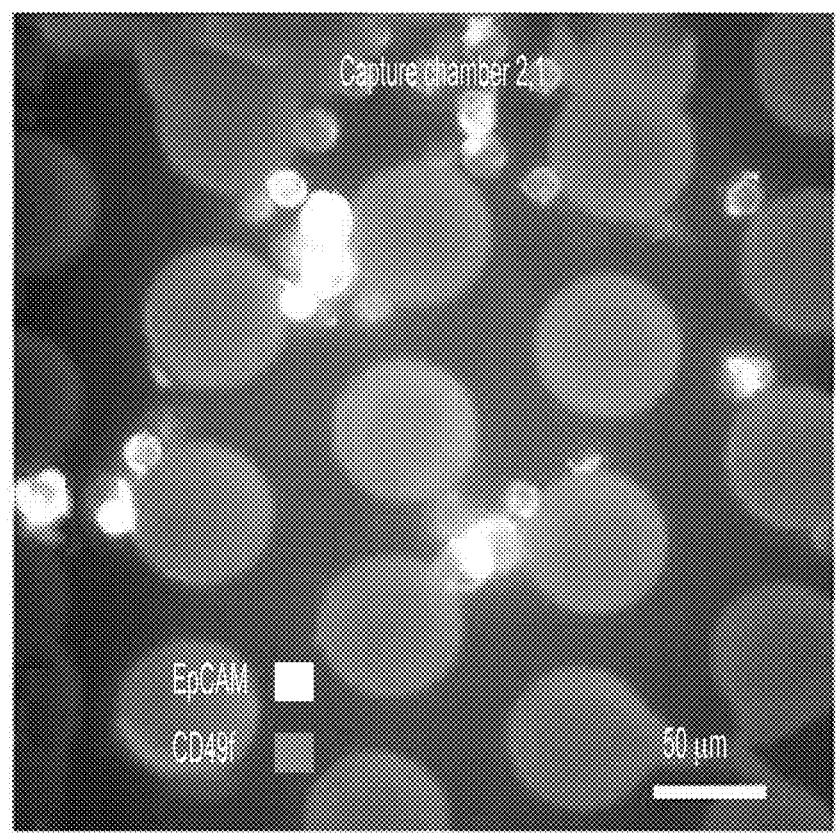
Figure 5F:
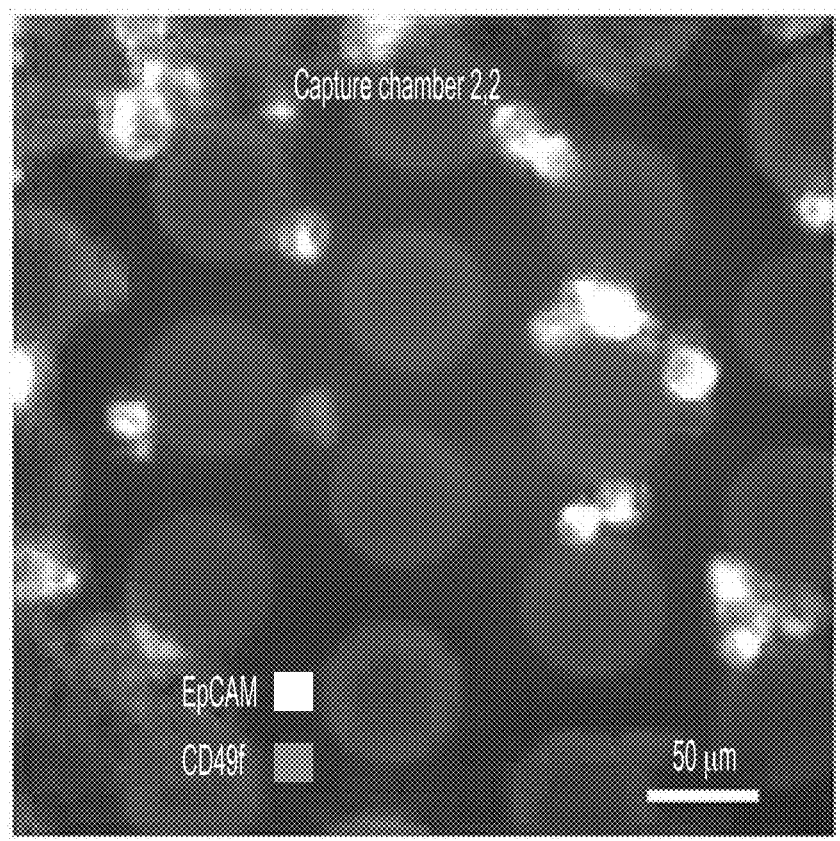
Figure 5G:
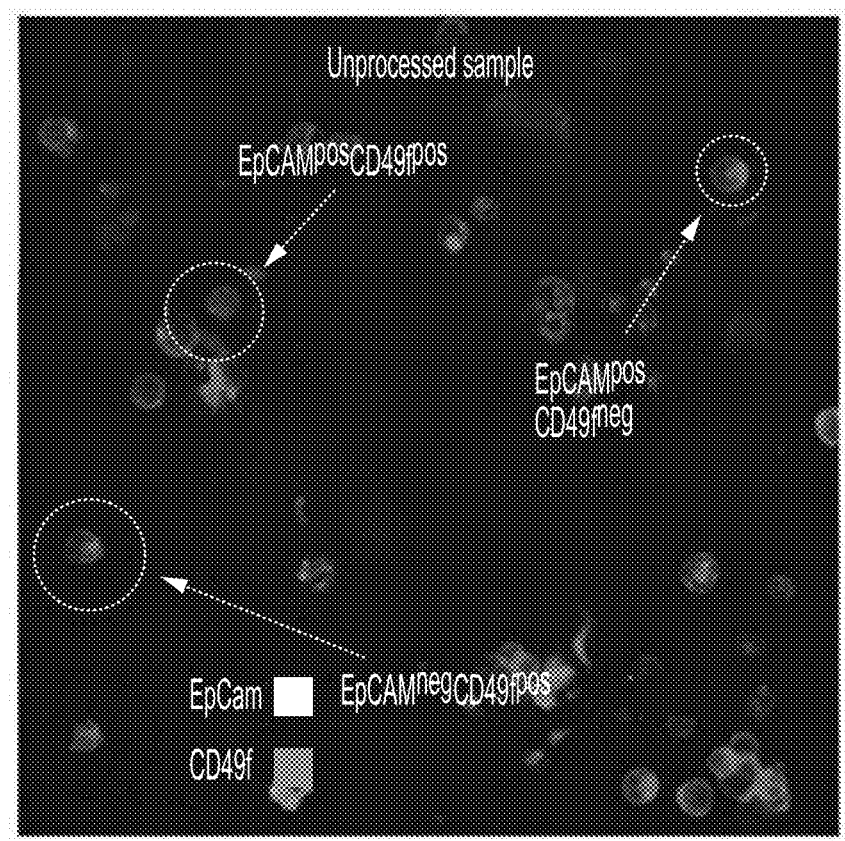
Figure 5H:
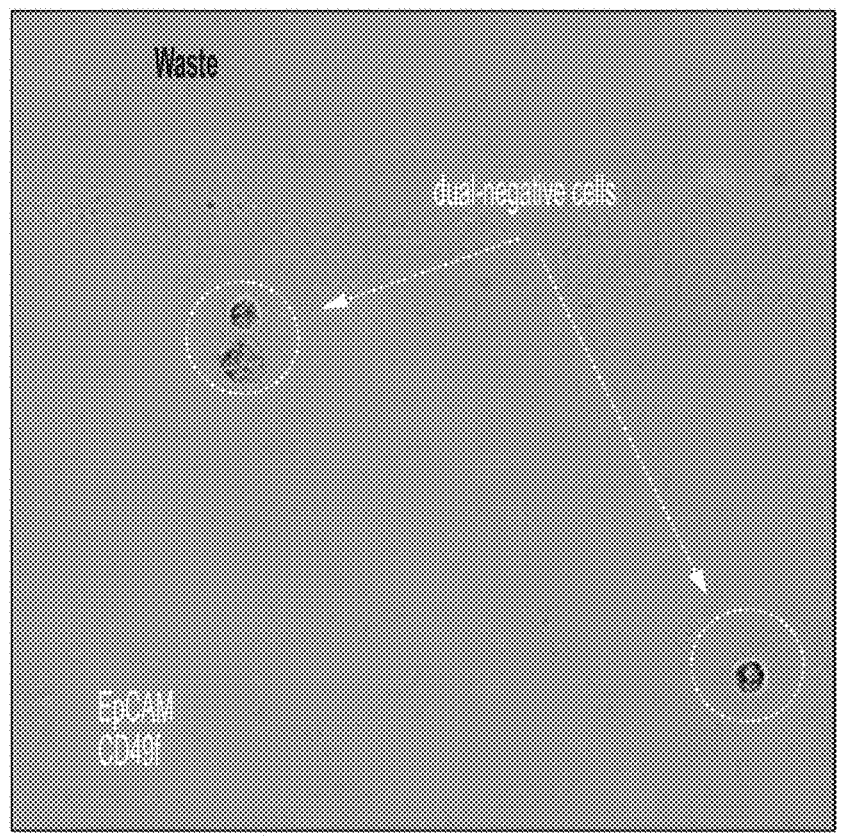

FIGS. 5a-h show examples of immunophenotyping of tumor cell mixtures. FIG. 5a depicts an exemplary schematic showing the specific antibody arrangement in the designed microarray. Anti-EpCAM 502A,D and anti-CD49f 502B,C antibodies are immobilized in chambers with a checkerboard pattern to fractionate mixtures of MCF7 (EpCAM$^{pos}$CD49f$^{neg}$), SK-BR-3 (EpCAM$^{pos}$CD49f$^{pos}$), and MDA-MB-231 (EpCAM$^{low/neg}$CD49f$^{pos}$) and dual-negative (EpCAMnegCD49f$^{neg}$) cells, which are discharged from the waste outlet. FIG. 5b depicts an exemplary Comparison of the measured frequency (colored bar) and the mix ratios (overlaid unshaded bar) of different cancer cell lines in control samples. Four control samples were prepared by mixing MCF7, SK-BR-3, and MDA-MB-231 cancer cell lines at ratios of 1:1:1, 3:1:1, 1:3:1, and 1:1:3. FIGS. 5c-h depict exemplary representative two-channel fluorescence images of the captured cells post labeled with a cocktail of Alexa Fluor 594 anti-EpCAM and Alexa Fluor 488 anti-CD49f antibodies in FIG. 5d) chamber 1,1 (EpCAM$^{pos}$), FIG. 5e) chamber 1,2 (EpCAMnegCD49f$^{pos}$), FIG. 5f) chamber 2,1 (CD49f$^{pos}$), and iv) chamber 2,2 (CD49f$^{neg}$EpCAM$^{pos}$). FIG. 5g) The fluorescence image of the unprocessed sample stained with the same fluorophore-conjugated antibodies show all combinatorial immunophenotypes (EpCAM$^{pos}$CD49f$^{pos}$, EpCAM$^{pos}$CD49f$^{neg}$, and EpCAM$^{low/neg}$CD49f$^{pos}$). FIG. 5h) A fluorescence image of cells (EpCAM$^{neg}$CD49f$^{neg}$) found in the waste collected from our device. Post labeling of cells against the two antibodies produced no fluorescence signal indicating the dual-negative immunophenotype of these cells.

For controlled experiments to validate our assay, we employed human cancer cell lines with differing antigen expression. We cultured three breast cancer cell lines (MCF7, SK-BR-3, and MDA-MB-231) and selectively functionalized cell capture chambers with two different antibodies (anti-EpCAM and anti-CD49f antibodies) specifically chosen to target antigens that are differentially expressed by those breast cancer cell lines: MCF7: EpCAM$^{pos}$CD49f$^{neg}$, SK-BR-3: EpCAM$^{pos}$CD49f$^{pos}$, MDA-MB-231: EpCAMlow/$^{neg}$CD49f$^{pos}$ with a secondary EpCAM$^{low/neg}$CD49f$^{neg}$ immunophenotype. To distinguish these immunophenotypes, we arranged the anti-EpCAM and anti-CD49f antibodies in cell capture chambers as a 2×2 checkerboard pattern (FIG. 5a), which enabled us to screen cells for all possible combinations of EpCAM and CD49f expressions. Based on the individual cell counts from the coded electrical sensors on the microfluidic device (Table 1), we were able to calculate the fraction of cells captured in each cell capture chamber (Table 2) and use the measured cell capture statistics to calculate the prevalence of each combinatorial immunophenotype (Table 3) in the sample.

The calculation of the target subpopulation fractions in the cell mixture from the electrical data is shown in Table 3:

| Combinatorial immunophenotype | Fraction |
|---|---|
| EpCAM$^{pos}$CD49f$^{pos}$ | $1 - p_{12} - p_{22} - (p_{1end} + p_{2end})/2$ |
| EpCAM$^{pos}$CD49f$^{neg}$ | $p_{22}$ |
| EpCAM$^{neg}$CD49f$^{pos}$ | $p_{12}$ |
| EpCAM$^{neg}$CD49f$^{neg}$ | $(p_{1end} + p_{2end})/2$ |

To test our assay's performance in identifying subpopulations with different antigen expressions, we processed suspensions of MCF7, SK-BR-3, and MDA-MB-231 cancer cells mixed at varying ratios as heterogeneous control samples at a flow rate of 80 μm s$^{-1}$. Our electronic results on the immunophenotype composition of different cell mixtures were consistently in good agreement with the designed mix ratios (FIG. 5b). The differences were mainly due to coexpression of the same immunophenotype by two different cancer cell lines, e.g., MDA-MB-231 cells also express EpCAM, at a low concentration, and were counted in the EpCAM$^{pos}$CD49f$^{pos}$ immunophenotype that was interpreted as SK-BR-3. Nevertheless, this is not a fundamental problem as measurements can be computationally corrected to accommodate crosstalk between immunophenotypes based on projected antigen coexpression rates of target cell subtypes in a given population. To independently validate cell immunophenotype discrimination by our assay, we characterized the expression of tumor cells captured on the chip via fluorescence microscopy after post labeling them against both EpCAM and CD49f From the dual-channel fluorescence images of stained cells, differences in the composition of cells captured in different chambers could clearly be observed: Anterior cell capture chambers in the microfluidic cascade (i.e., chambers 1,1 and 2,1) received the full sample composition and captured cells that expressed the target antigen (i.e., EpCAM for chamber 1,1 (FIG. 5c) and CD49f for chamber 2,1 (FIG. 5e)). In both anterior cell capture chambers, dual-expressor cells could also be observed as the expression of another antigen did not interfere with the cell immunocapture. In contrast, cells captured in posterior chambers contained only single-expressor cells with the antigen targeted by the capture antibody immobilized in the corresponding capture chamber (CD49f for chamber 1,2 (FIG. 5d) and EpCAM for chamber 2,2 (FIG. 5O). The lack of dual-expressor cells in the posterior chambers is due to the fact that posterior cell capture chambers received only a portion of the sample that was already depleted of cells expressing the antigen targeted by the anterior chamber. As a control, we labeled cells in the unprocessed (input) mixture and also in the waste (output) with the same fluorophore-conjugated antibodies and observed cells in the unprocessed sample expressed all possible immunophenotypes (FIG. 5g), while cells in the waste were all dual-negative expressing neither EpCAM nor CD49f (FIG. 5O. Taken together, these results demonstrated a successful fractionation of a heterogeneous sample into different cell capture chambers based on the cell immunophenotype and validated the platform for combinatorial phenotyping of cell populations.

Figure 6A:
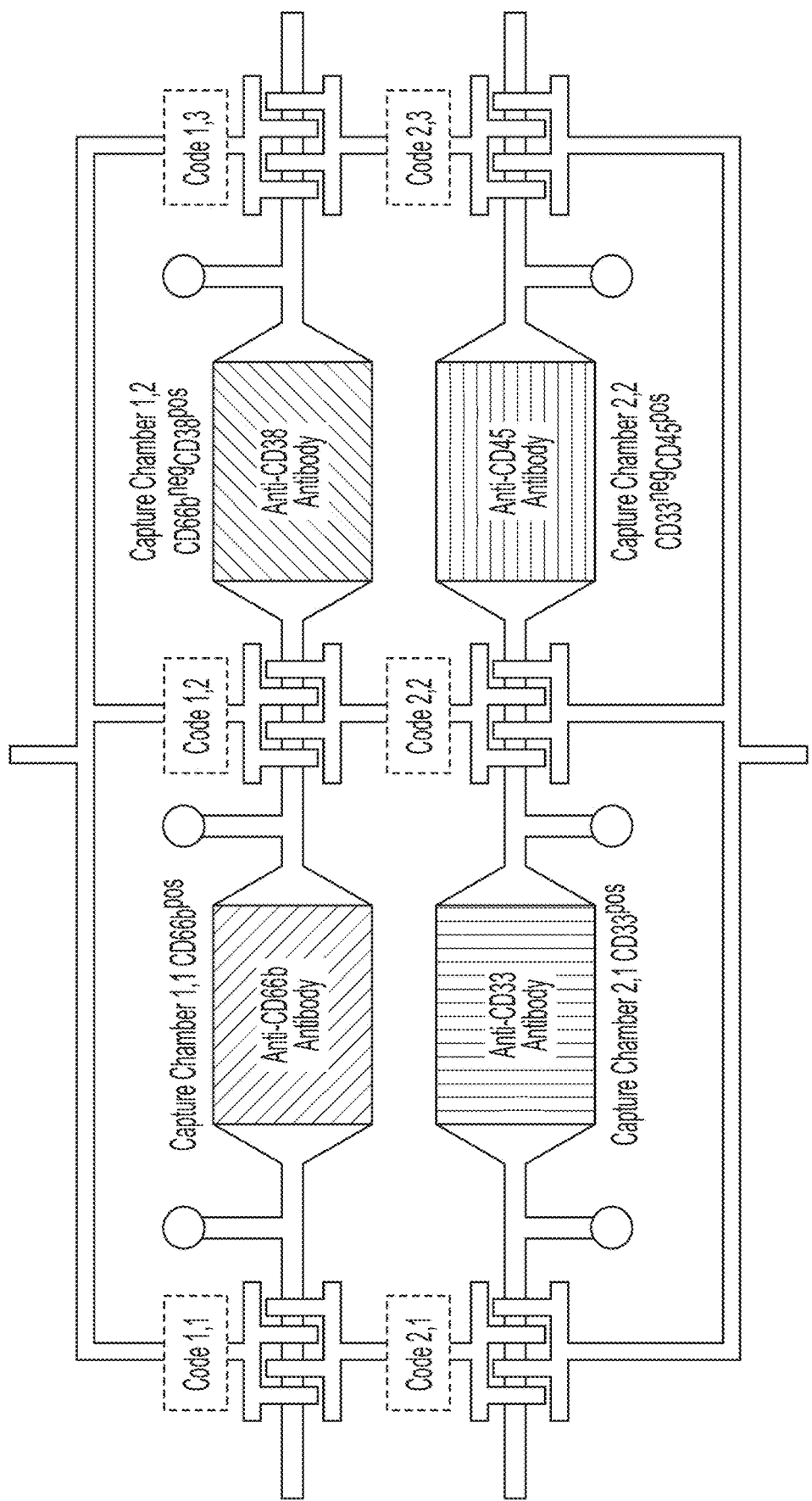
FIGS. 6a, 6b, 6c, 6d, 6e, and 6f illustrate an example of immunophenotyping of leukocytes, according to embodiments of the present devices and methods.
Figure 6B:
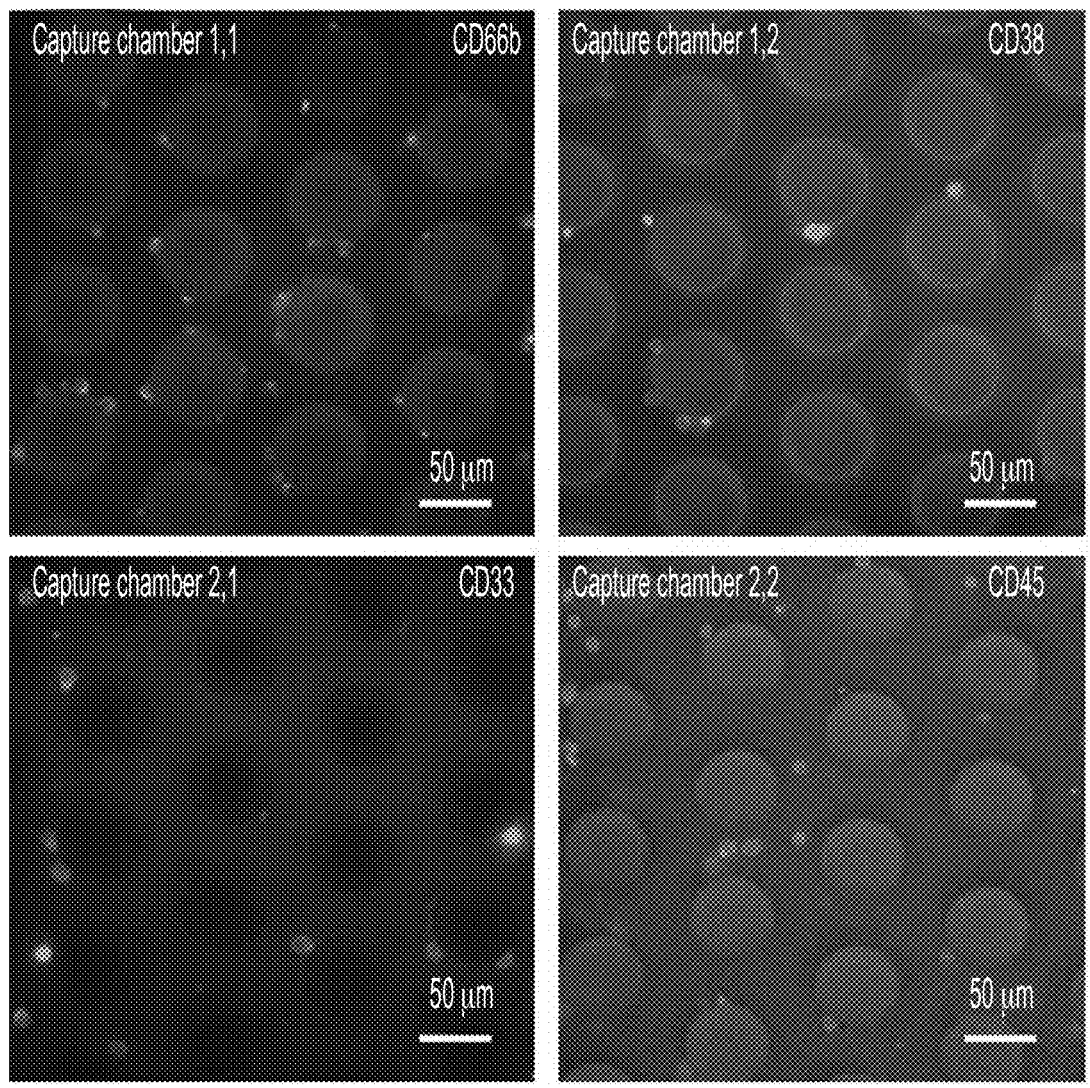
Figure 6C:
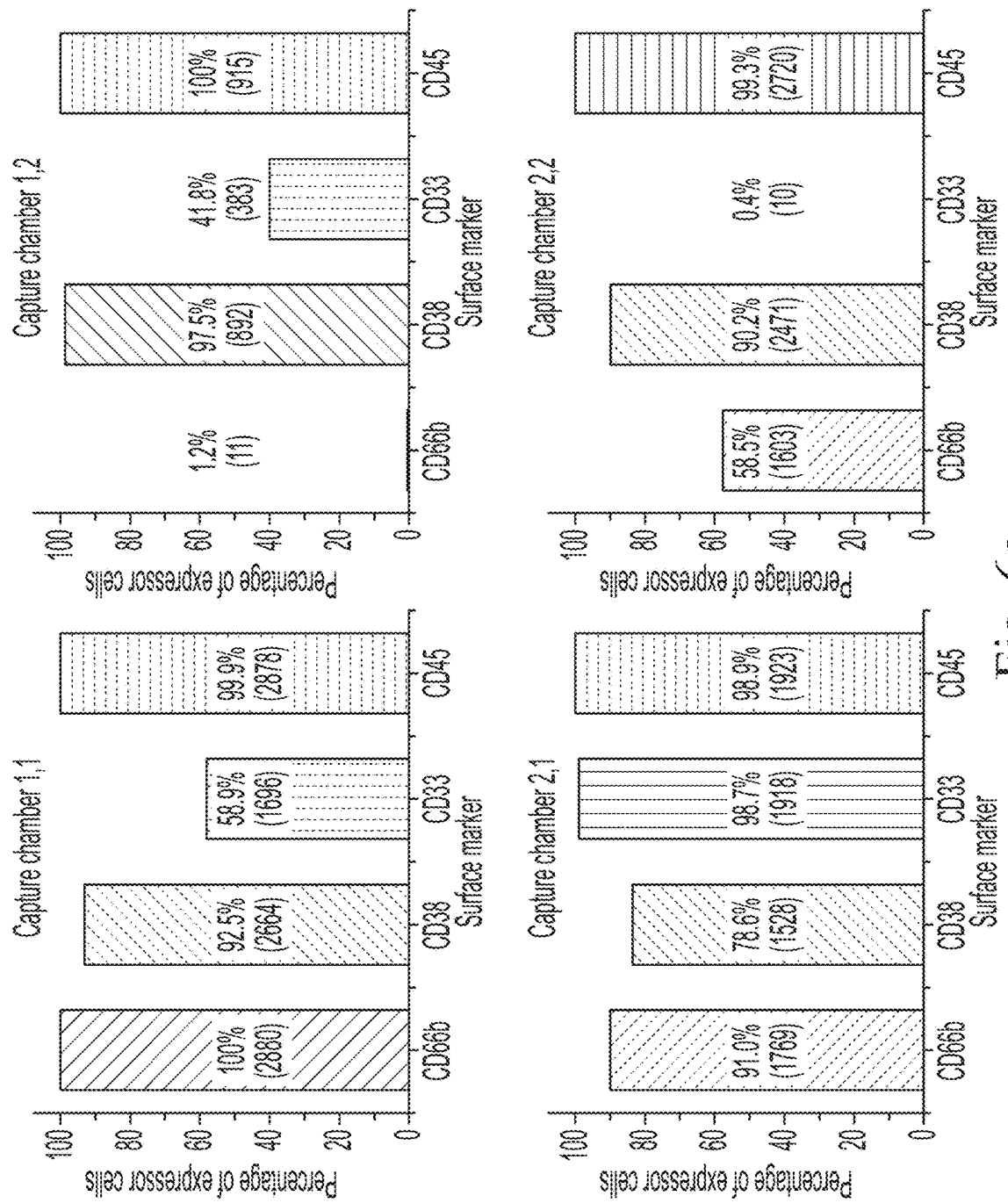
Figure 6D:
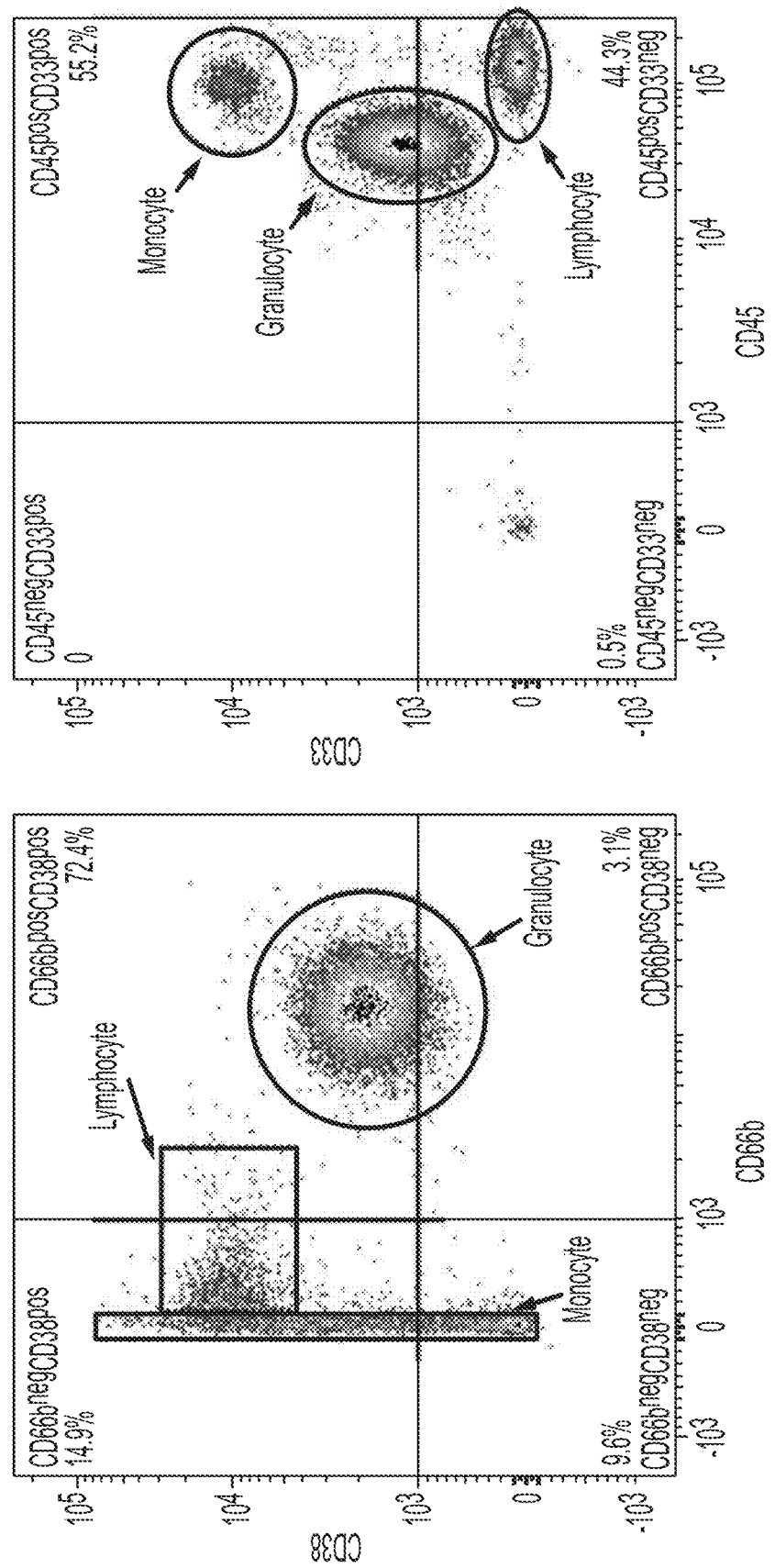
Figure 6E:
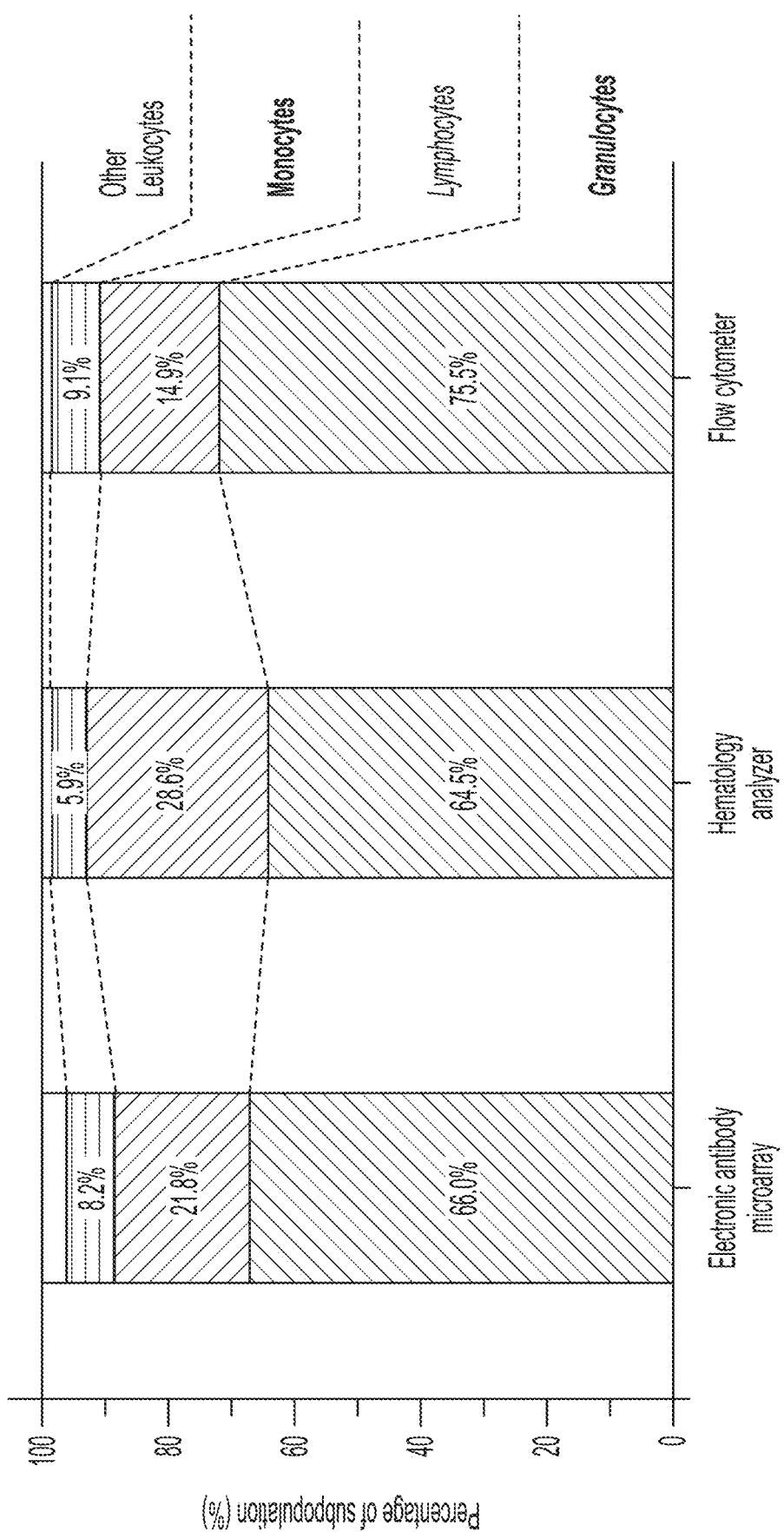
Figure 6F:
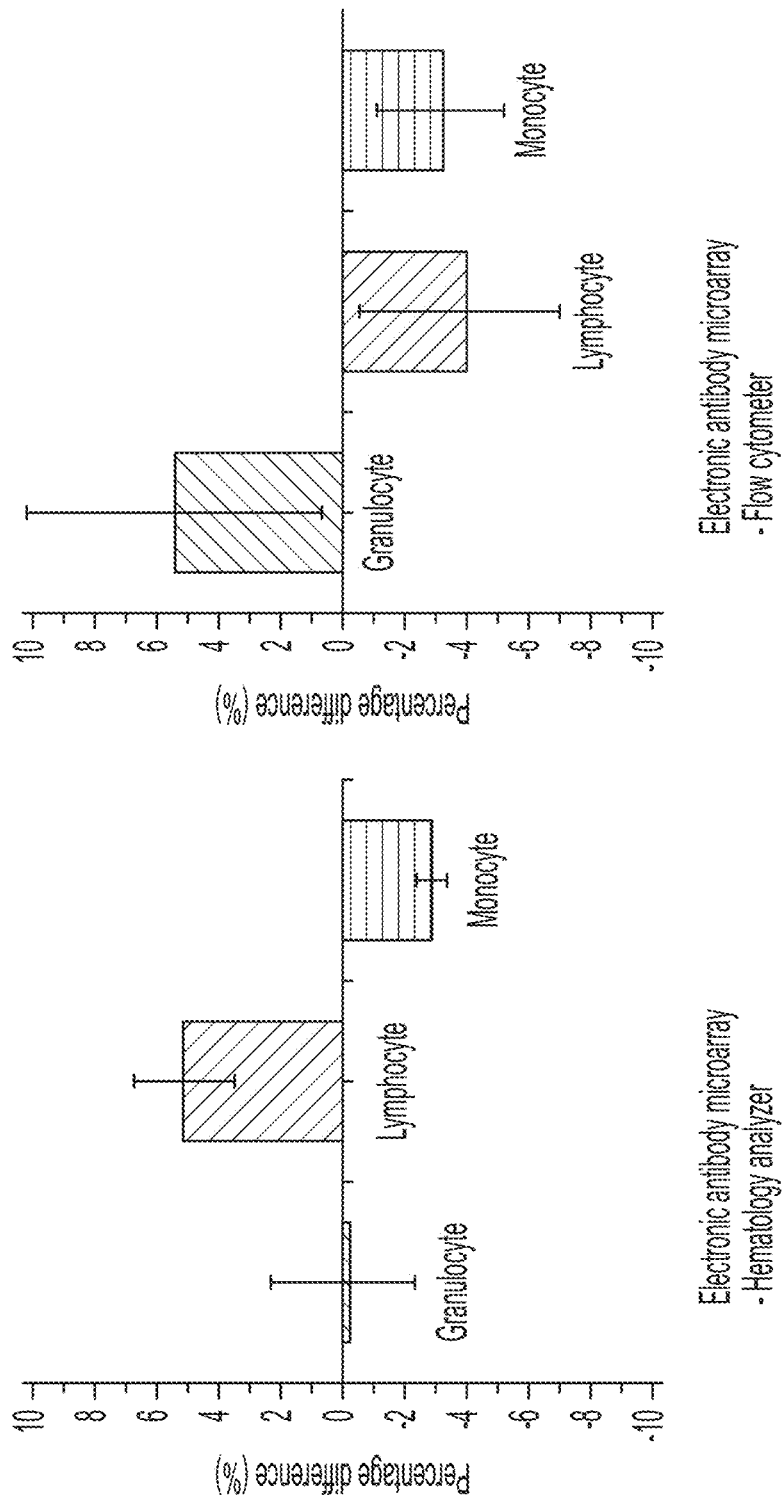

FIGS. 6a-f show examples of immunophenotyping of leukocytes. FIG. 6a depicts a schematic diagram showing the specific antibody arrangement in the microarray. Microfluidic cell capture chambers were functionalized with anti-CD66b, anti-CD38, anti-CD33, and anti-CD45 antibodies to fractionate leukocytes into granulocytes, lymphocytes, and monocytes. FIG. 6b shows single-channel fluorescent images showing surface marker expressions on the captured cells in different microfluidic chambers. The images show all captured cells expressing the antigen targeted by the corresponding capture chamber. FIG. 6c shows immunoexpression of cells captured in each microfluidic chamber. All of the captured cells were labeled with fluorophore-conjugated antibodies against all four antigens, and the frequency of each immunophenotype was calculated for each cell capture chamber. Each bar in the plots shows the measured frequency and the actual cell count for the immunophenotype in the corresponding capture chamber. FIG. 6d shows classification of leukocyte subpopulations with flow cytometry. The density scatter plots show frequencies of the subpopulations for each immunophenotype. The gates in the plots were set based on the prior tests with fluorophore-labeled calibration beads. The measurements were grouped as granulocyte, lymphocyte, or monocyte based on the cell hierarchy population analysis from the forward scatter-side scatter (FSC-SSC) plot (see FIG. 14, which is an FSC-SSC scatter plot obtained from the flow cytometry analysis of the leukocytes used in the study. Gates used for designating leukocyte subpopulations are shown on the plot.) for better illustration. FIG. 6e shows the frequency of leukocyte subpopulations measured by our device, a commercial hematology analyzer, and a commercial flow cytometer in matched samples. FIG. 6f shows the average difference in the measurement of leukocyte subpopulations using our device versus the hematology analyzer (left) and the flow cytometer (right). Error bars represent standard deviation.

Immunophenotyping of Leukocytes. To demonstrate the relevance of our assay for point-of-care testing, we designed an assay to measure the composition of leukocytes in a blood sample. To distinguish different leukocyte subpopulations, we functionalized our device with four different antibodies (anti-CD66b, anti-CD38, anti-CD33, and anti-CD45) against antigens differentially expressed among leukocytes. Importantly, the spatial arrangement of antibodies on the device (FIG. 6a) was specifically designed to distinguish different leukocyte subtypes with distinct immunophenotypes, namely granulocytes, lymphocytes, and monocytes: In one of the microfluidic paths, antibodies were immobilized in a sequence, where the anti-CD66b was followed by the anti-CD38. Under this arrangement, cells captured in the anterior chamber (i.e., CD66b$^{pos}$ immunophenotype) were considered as granulocytes, while cells in the posterior chamber (i.e., CD66b$^{neg}$CD38$^{pos}$ immunophenotype) were considered as lymphocytes. In the other microfluidic path, the anti-CD33 was followed by the anti-CD45. Because CD33 is a surface marker used for identifying monocytes, that is also expressed by granulocytes, we interpreted cells captured in the anterior chamber (i.e., CD33$^{pos}$ immunophenotype) as a mixed population of monocytes and granulocytes, while cells in the posterior chamber (i.e., CD33$^{neg}$CD45$^{pos}$ immunophenotype) were considered as granulocytes and lymphocytes. By processing electrical sensor data, we could determine the capture statistics for each immunophenotype (Table 4) and calculate the frequency of each leukocyte subpopulation (Table 5) in the blood sample.

The immunophenotype, calculation of the fractions, and the types of cells captured in each chamber and noncaptured cells discharged into the waste is shown in Table 4:

| Chamber | Immunophenotype | Fraction | Cell type |
| --- | --- | --- | --- |
| Chamber 1, 1 | CD66b$^{pos}$ | $p_{11} = (c_{11} - c_{12})/c_{11}$ | Granulocytes |
| Chamber 1, 2 | CD66b$^{neg}$CD38$^{pos}$ | $p_{12} = (c_{12} - c_{13})/c_{11}$ | Lymphocytes |
| Outlet 1 | CD66b$^{neg}$CD38$^{neg}$ | $p_{1end} = c_{13}/c_{11}$ | |
| Chamber 2, 1 | CD33$^{pos}$ | $p_{21} = (c_{21} - c_{22})/c_{21}$ | Monocytes + granulocytes |
| Chamber 2, 2 | CD33$^{neg}$CD45$^{pos}$ | $p_{22} = (c_{22} - c_{23})/c_{21}$ | Lymphocytes + granulocytes |
| Outlet 2 | CD33$^{neg}$CD45$^{neg}$ | $p_{2end} = c_{23}/c_{21}$ | Other leukocytes |

The parametric calculation of the fraction of each leukocyte subtype in the leukocyte suspension is shown in Table 5:

| Leukocyte subtype | Fraction |
| --- | --- |
| Granulocytes | $p_{11}$ |
| Lymphocytes | $p_{12}$ |
| Monocytes | $1 - p_{11} - p_{12} - p_{2end}$ |

Figure 15:
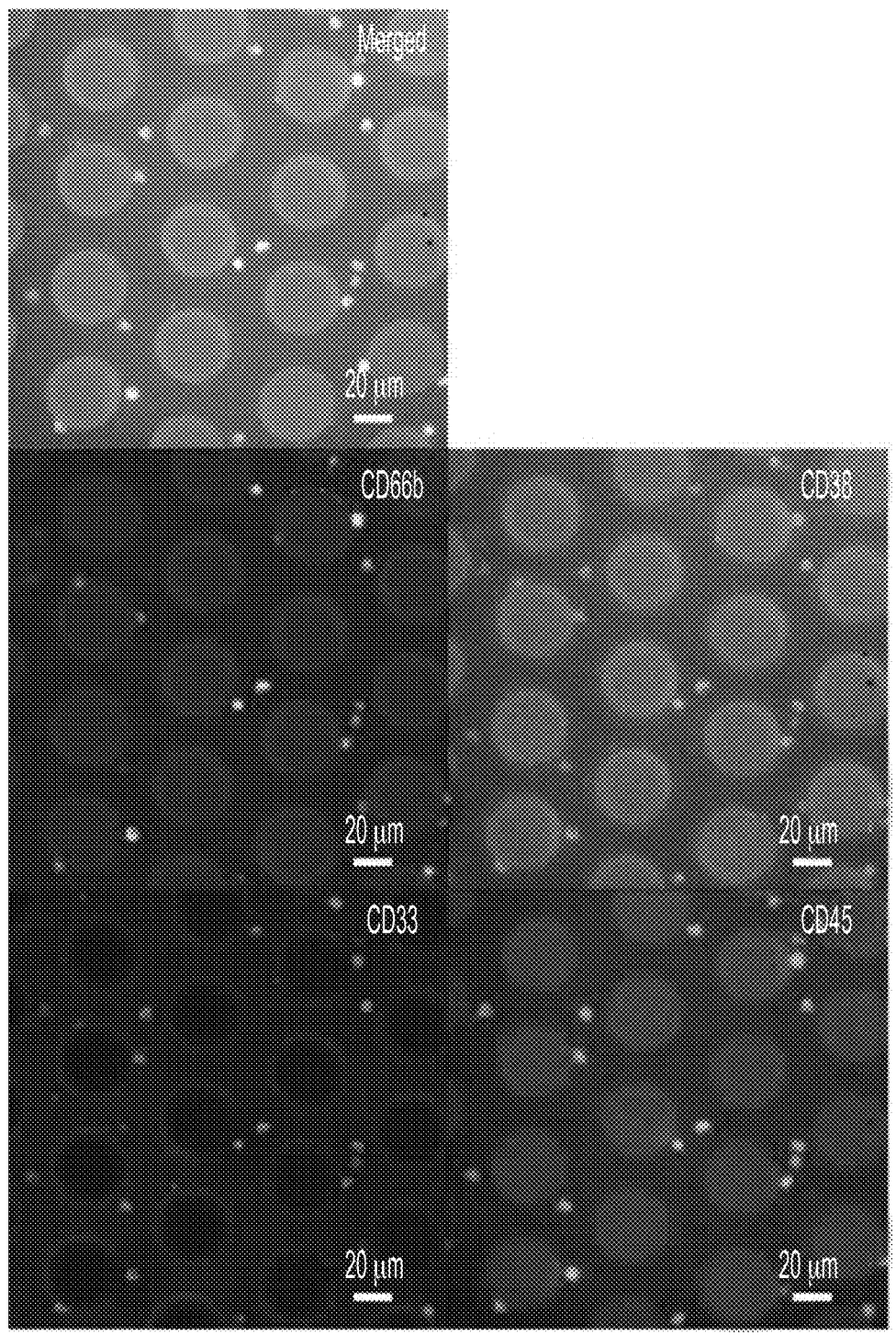
FIG. 15 shows immunofluorescence characterization of cell populations captured in microfluidic chambers.

We applied our technology on blood samples collected from consenting donors and validated our results by fluorescently labeling and imaging of leukocytes captured on our device. Following the lysis of erythrocytes, ≥4000 leukocytes were processed using our assay in 10-15 min at a flow rate of 80 μm s$^{-1}$. Following the completion of the assay, cells were immunolabeled on the chip with a cocktail of Alexa Fluor 594 anti-CD66b, Alexa Fluor 488 anti-CD38, Alexa Fluor 647 anti-CD33, and Brilliant Violet 421 anti-CD45 antibodies and characterized with a fluorescence microscope. Fluorescence measurements confirmed that virtually all captured leukocytes expressed the surface antigen targeted by the corresponding capture chamber (FIG. 6b). By imaging all leukocytes on the chip in different fluorescence channels (FIG. 15), we measured the frequency of expression for all four antigens in each capture chamber (FIG. 6c). This complete picture of cell composition demonstrated that 1) our microfluidic device was very efficient in capturing target cells, and 2) cell population captured in different chambers showed drastic differences in their expression profile, further confirming successful sample fractionation into distinct subpopulations. FIG. 15 shows the immunofluorescence characterization of cell populations captured in microfluidic chambers. These representative fluorescence images show a group of leukocytes captured in the microfluidic chamber functionalized with anti-CD33 antibody. The captured cells were post-labeled with a cocktail of Alexa Fluor 594 anti-CD66b, Alexa Fluor 488 anti-CD38, Alexa Fluor 647 anti-CD33, and Brilliant Violet 421 anti-CD45 antibodies. Similar images were also taken in other capture chambers by scanning fluorescence microscopy. Finally, by counting the cells positive in each fluorescence channel, the frequency of different immunophenotypes was calculated for each capture chamber.

Figure 14:
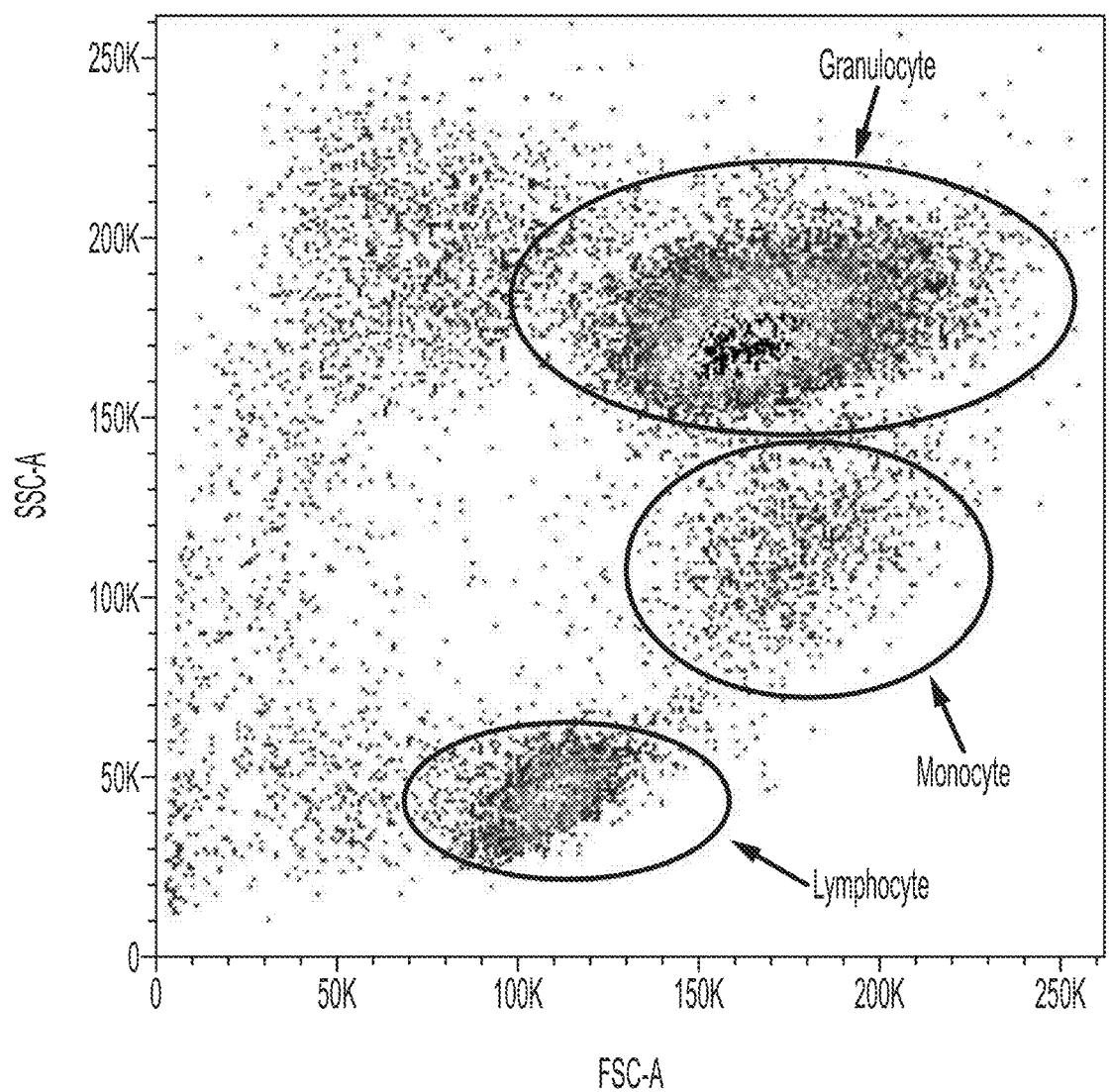
FIG. 14 shows an FSC-SSC scatter plot obtained from the flow cytometry analysis of leukocytes.

To assess the performance of our technique for blood analysis, we benchmarked our results against measurements from established hematology techniques. Matching blood samples were processed with a commercial benchtop hematology analyzer (CELL-DYN Ruby, Abbott) to obtain a complete blood count and also with a flow cytometer (LSRFortessa, Becton, Dickinson and Company). For the flow cytometry, the leukocyte suspension was fluorescently labeled against the same set of antigens employed in our assay, and the results were gated based on preconfigured values for leukocyte classification to calculate the frequency of each subpopulation (FIG. 6d and FIG. 14). Considering the differences between the complete blood count and flow cytometry results, our results are in agreement with both techniques (FIG. 6e); the percentage of $CD66b^{pos}$ cells (granulocytes) measured by our device, hematology analyzer, and flow cytometer were 66.0%, 64.5%, and 75.5%, respectively; the percentage of $CD66b^{neg}CD38^{pos}$ cells (monocytes) was measured as 21.8% with the antibody microarray, 28.6% with the hematology analyzer, and 14.9% with the flow cytometer; the frequency of the $CD33^{pos}$ cells was determined by our device to be 43.0% versus 55.2% from the flow cytometer. Our repeated measurements on blood samples collected from different donors showed that our device could accurately identify leukocyte subpopulations with an average of ≤6% difference from complete blood count and flow cytometry results (FIG. 6f). Observed differences between these measurements should be expected due to several factors: 1) transduction modalities of the three methods are fundamentally different, leading to entirely different discrimination criteria to classify different subpopulations, 2) artifacts are unavoidably introduced during different sample preparation steps required for different techniques, e.g., erythrocyte residues in the lysed samples or cell loss during centrifugation processes.

The electronic antibody microarray, introduced in this work, is a viable immunophenotyping assay with several advantages over existing methods for the analysis of cell populations. First, our technique is label-free. In a typical flow cytometry assay, the samples have to be prelabeled with fluorophore-conjugated antibodies to transduce chemical information into optical signals, while unlabeled cells can directly be introduced into our assay for analysis. The label-free operation not only makes our approach well suited for settings where sample preparation is not feasible but also reduces the total assay time, thereby increasing its practical utility. Second, our assay directly reports immunophenotyping results as electrical data. Compared to optical systems, which require both optical and electrical components, our platform can be coupled with an electronic circuit that can both drive and read the on-chip sensors, reducing both the system complexity and size. Compared to conventional electrical cytometry that measures physical properties of cells (e.g., size and electrical parameters), our technique probes well-established and more specific biochemical markers on the cell membrane, which cannot be probed through electrical means otherwise. On-chip multiplexing of electrical data enables an efficient acquisition, storage, transmission, and analysis of the assay results. In fact, computational analysis of the assay results could be performed in real-time (≈1000 cells s$^{-1}$) using deep learning algorithms. Overall, our platform operates as simple as a Coulter counter supported with more advanced software to interpret its results. Third, our assay is both flexible and scalable to screen for a specific and larger number of antigen combinations, respectively. Flow cytometers are limited in the number of antigens that can be probed simultaneously due to spectral crosstalk in the detectors. In contrast, our platform can add more capture chambers and sensors without affecting the performance of existing sensors. Compared to conventional antibody microarrays, on the other hand, our assay can identify subpopulations expressing different antigen combinations by sequentially subjecting the cells to different antibodies. Taken together, label-free immunophenotyping of cell populations against multiple targets on an electronic disposable chip presents an opportunity in global health and telemedicine applications for cell-based diagnostics and health monitoring.

To selectively modify each chamber in the antibody microarray with a specific antibody, we apply a set of auxiliary functionalization ports 202A-F in the PDMS layer, as shown in FIG. 2d. The auxiliary holes 202A-F can be either directly added on top of the capture chamber region 204, or indirectly connected with the inlet 205 and outlet 206 of the capture chamber through the microfluidic path to exclusively deliver the functionalization reagents to the desired cell capture chamber. The size of the auxiliary ports 202A-F may be adjusted to any size based on the available area on the microfluidic device. The antibodies are then introduced through the corresponding auxiliary ports 202A-F and immobilized in the capture chamber 204 using any protocol for antibody crosslinking/self-assembly monolayer forming on the silicon-based substrate (e.g., APTES-glutaraldehyde-antibody, MPTMS-GMBS-neutravidin-biotinylated antibody, Tris-HCl-Tris-antibody, etc.)

Figure 7:
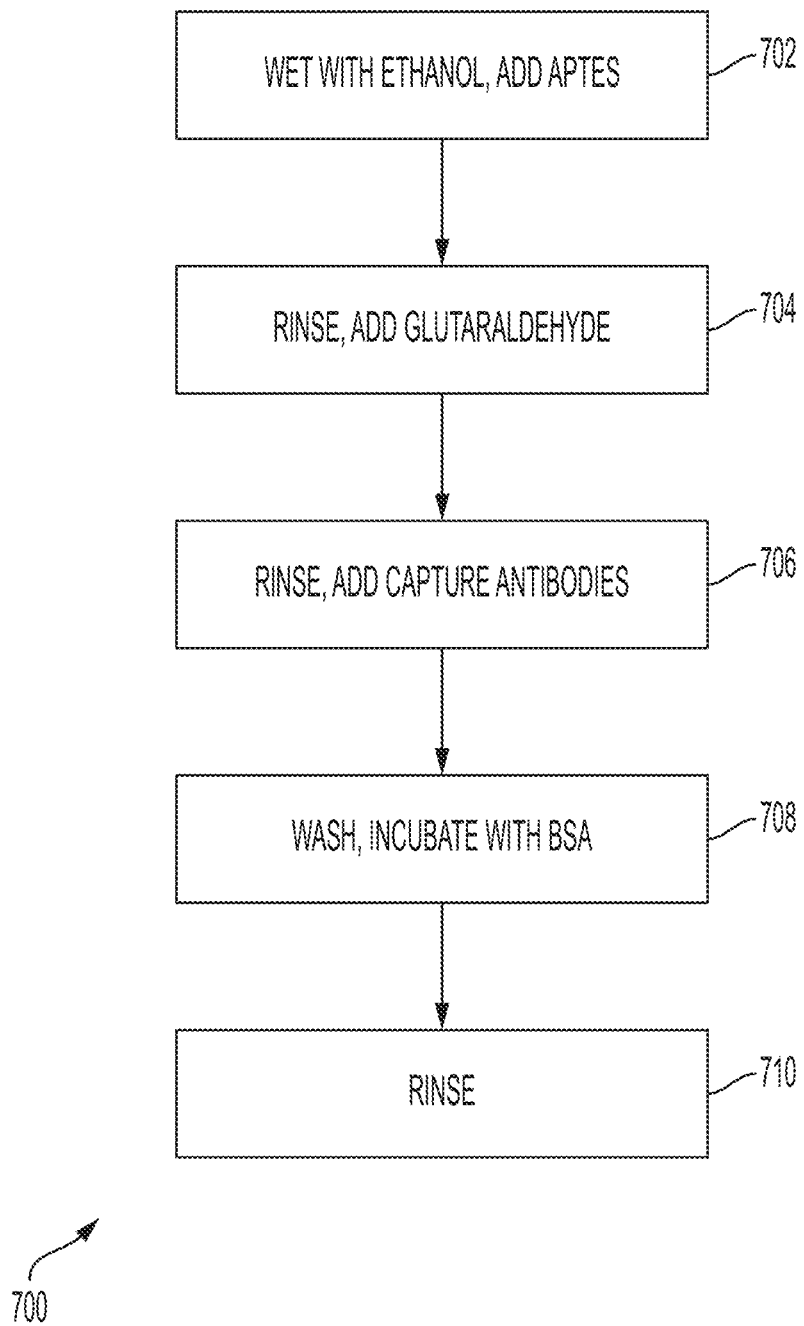
FIG. 7 illustrates an exemplary flow diagram of an immobilization protocol, according to embodiments of the present devices and methods.
Figure 16:
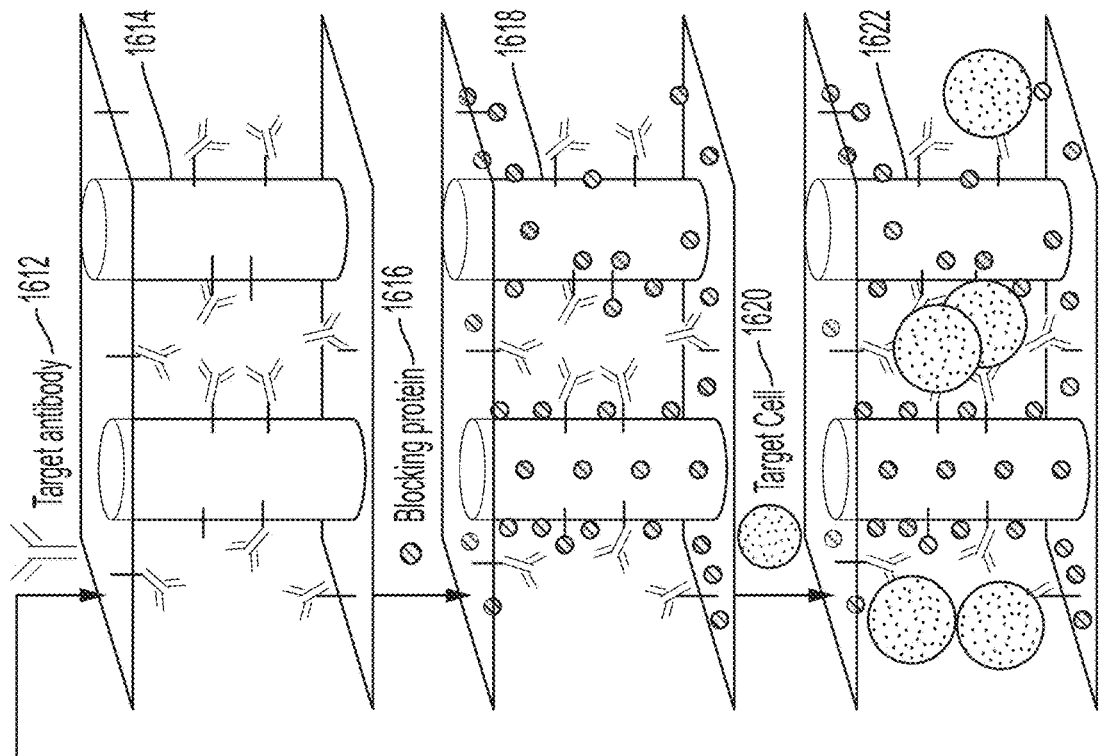
FIG. 16 shows a schematic showing the step-by-step functionalization process and specific chemistry used to immobilize antibodies on the device surface.
Figure 16:
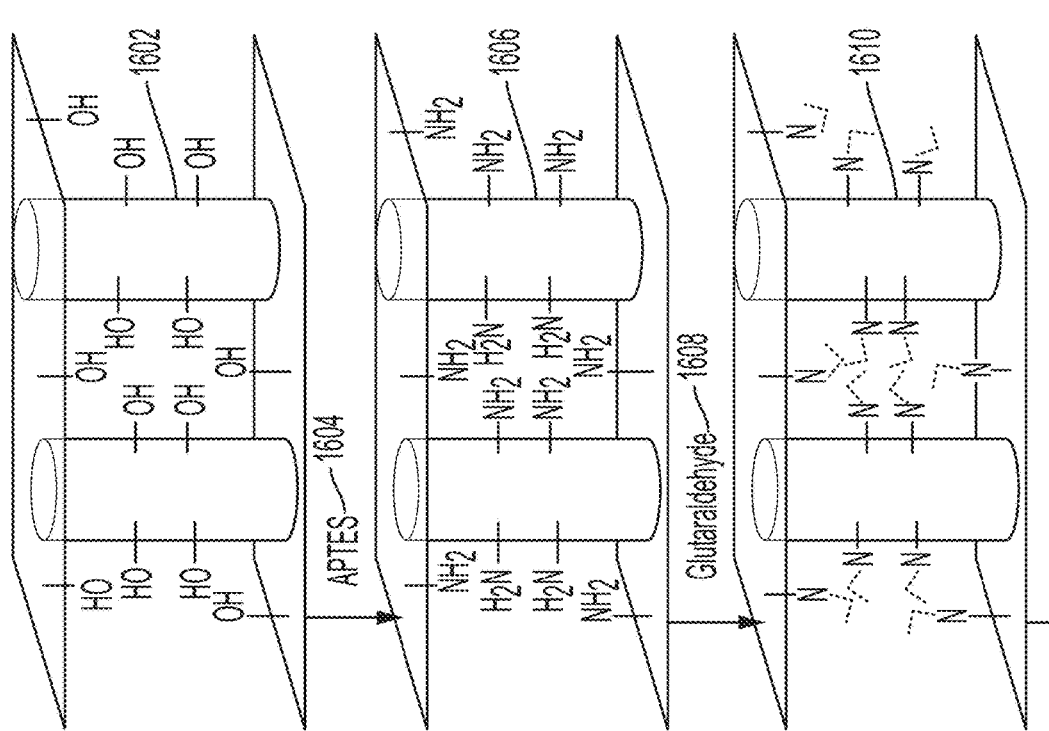

One immobilization protocol example, which may be used in embodiments of the device is shown in FIG. 7. It is best viewed in conjunction with FIG. 16, which is a schematic showing the step-by-step functionalization process and specific chemistry used to immobilize antibodies on the device surface We employed a chemical modification protocol 700 at, for example, room temperature to functionalize the cell capture chambers with antibodies. At 702, the initial microfluidic device 1602 is wetted with ethanol, and within 10 minutes of the PDMS-glass bonding, APTES 1604 in ethanol (2% v/v) is introduced to the device and incubated for 30 minutes 1606. At 704, the device is rinsed with ethanol and DI water, and a glutaraldehyde 1608 solution in de-ionized water (1% v/v) is introduced and incubated for 30 minutes 1610. At 706, the device is rinsed with DI water and PBS, and target capture antibodies 1612 in PBS are introduced into the cell capture chambers and incubated for 1 hour 1614. At 708, the device is washed with PBS to remove unbound antibodies, and the cell capture chambers is incubated with BSA blocking buffer (protein) 1616 for 1 hour to block the non-specific binding sites 1618. At 710, the device is rinsed with PBS to complete the functionalization process. During use, target cells 1620 may be introduced into the cell capture chambers and may adhere to the surfaces of the chamber 1622.

After the capture chamber modification process, the auxiliary ports may be sealed to prevent leakage during the assay, and the device is interfaced via normal microfluidic inlet and outlet.

The auxiliary holes for the cell capture chamber can be designed either as "inlet-outlet" pairs or as inlet port only. When the outlet ports exist, the reagents from each chamber will come out from its dictated auxiliary outlet port; when there are inlet ports only, the common microfluidic inlet and outlet can be used as the exits of reagents.

The auxiliary holes may be designed for the antibody microarray with 1×1 structure, 1×N structure, M×1 structure, M×N structure, or any other rectangular or non-rectangular structure for different immunophenotyping applications.

The PDMS layer may be functionalized through the auxiliary ports first, and combined with glass substrates using vacuum or clamp sealing, or the PDMS layer can also be bonded with glass substrates first, and functionalized through the auxiliary ports later.

In the cell capture chambers, embodiments may include pillars to increase the cell capture area and to structurally support the cell capture chamber ceiling. The pillars form a staggered two-dimensional array to increase the likelihood of cell-pillar contact under laminar flow. The shape of the pillars may be any shape (spherical, semi-spherical, oval, bow-shape, triangle, rectangular, diamond, etc.), and the pillars can also be replaced by other structures (channels, tunnels, membranes, meshes, etc.) that can physically absorb/entrap or chemically crosslink the antibodies to increase the capture area, e.g., hydrogel, agar, SAM membrane.

Conclusion. Embodiments may include a microfluidic antibody microarray that can electrically report the frequency of target cell subpopulations in a sample. In our device, functionalized microfluidic chambers cascaded to produce different antibody combinations fractionate samples into its components, and an integrated sensor network transduces cell capture statistics into electrical data for label-free immunophenotyping. Remarkably, the application of our technique for the analysis of leukocyte subpopulations in blood samples produced comparable results with significantly more expensive and sophisticated commercial systems, both validating the assay accuracy and demonstrating its potential utility. All in all, we believe the ability to electrically screen cell immunophenotypes on a disposable chip that can be scaled and tuned for specific cell subsets could be transformative in cell-based diagnostics at the point-of-care and resource-limited scenarios.

Experimental Section. Chemicals and Materials: Ammonium chloride (NH4Cl), potassium bicarbonate (KHCO3), ethylenediaminetetraacetic acid (EDTA) tetrasodium salt, glutaraldehyde, and trichloro(octyl)silane were purchased from Sigma-Aldrich (St. Louis, MO), pure ethanol was purchased from Decon Labs, Inc. (Kings of Prussia, PA), APTES was purchased from Gelest, Inc. (Morrisville, PA), BSA was purchased from Thermo Scientific (Rockford, IL), 1×PBS was purchased from Mediatech (Manassas, VA), all chemicals are analytical grade. All water used for the experiment was deionized (DI) water. Alexa Fluor 594 anti-CD66b antibody (G10F5 clone), Alexa Fluor 488 anti-CD38 antibody (HIT2 clone), Brilliant Violet 421 anti-CD33 antibody (WM53 clone), Alexa Fluor 647 anti-CD45 antibody (2D1 clone), FITC anti-CD45 antibody (2D1 clone), anti-CD45 antibody (2D1 clone), anti-CD115 antibody (9-4D2-1E4 clone), Alexa Fluor 488 anti-CD115 antibody (9-4D2-1E4 clone), anti-EpCAM antibody (9C4 clone), anti-CD49f antibody (GoH3 clone), Alexa Fluor 594 anti-EpCAM antibody (9C4 clone), Alexa Fluor 488 anti-CD49f antibody (GoH3 clone), anti-CD66b antibody (G10F5 clone), anti-CD38 antibody (HIT2 clone), anti-CD33 antibody (WM53 clone), Alexa Fluor 647 anti-CD33 antibody (WM53 clone), Brilliant Violet 421 anti-CD45 antibody (2D1 clone), phycoerythrin (PE) anti-CD66b antibody (G10F5 clone), allophycocyanin (APC) anti-CD38 antibody (HIT2 clone), PE anti-CD45 antibody (2D1 clone), and APC anti-CD33 (WM53 clone) antibody were all purchased from Biolegend (San Diego, CA).

4 in. silicon wafers were purchased from University Wafer, Inc. (South Boston, MA), SU-8 2000 series photoresist was purchased from MicroChem (Westborough, MA), NR9-1500PY negative photoresist was purchased from Futurrex, Inc. (Franklin, NJ), PDMS elastomer Sylgard 184 was purchased from Dow Corning (Auburn, MI).

MCF7 (ATCC HTB-22), SK-BR-3 (ATCC HTB-30), and MDA-MB-231 (ATCC HTB-26) breast cancer cell lines were obtained from American Type Culture Collection (ATCC) (Manassas, VA), Dulbecco's modified Eagle's medium (DMEM) medium was purchased from Mediatech (Manassas, VA), fetal bovine serum (FBS) was purchased from Seradigm (Radnor, PA), 0.25% trypsin-EDTA was purchased from Life Technologies (Carlsbad, CA).

The blood samples were obtained via venipuncture from healthy donors' bodies using an informed consent process according to the Georgia Tech Institutional Review Board (IRB) protocol approved by Georgia Tech IRB.

Figure 8:
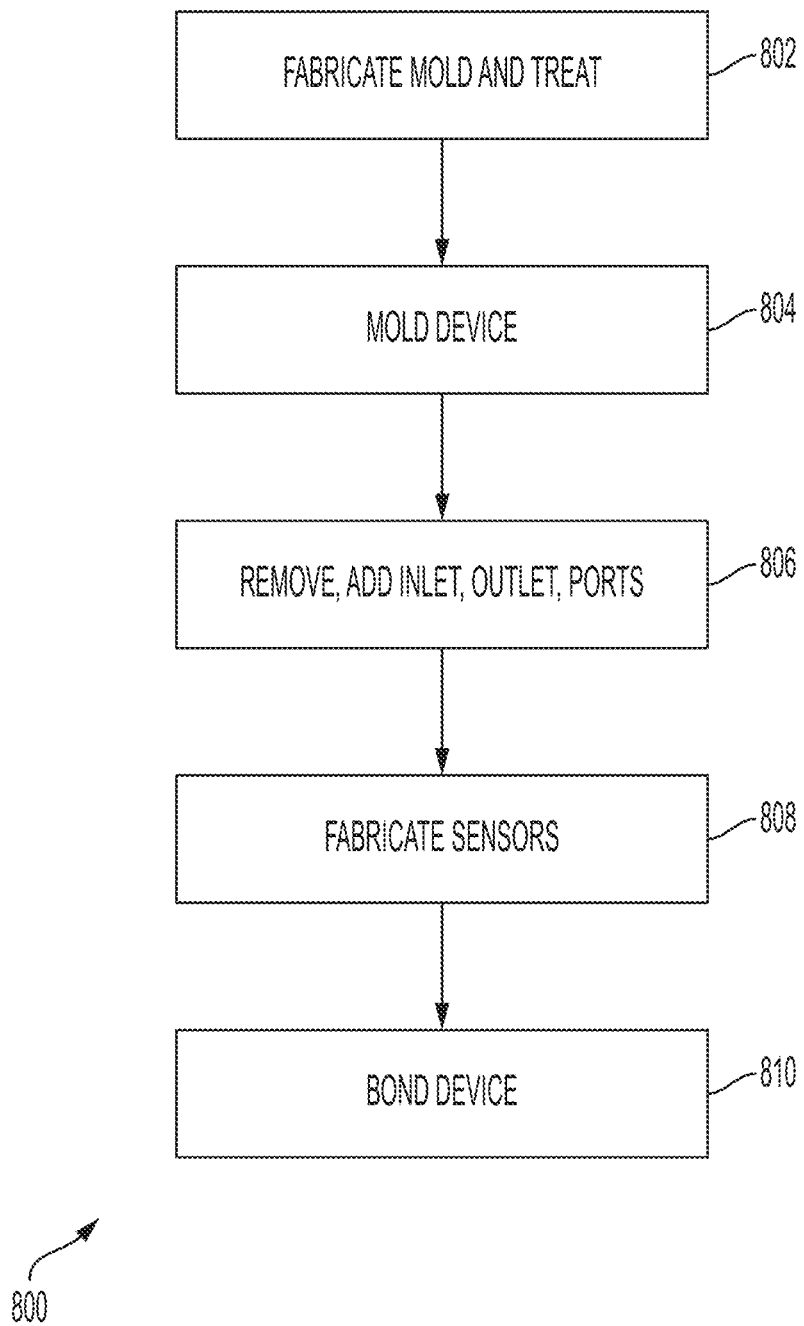
FIG. 8 illustrates an exemplary flow diagram of a process for fabricating embodiments of a microfluidic device, according to embodiments of the present devices and methods.

Fabrication of the Microfluidic Device: An exemplary process 800 for fabricating embodiments of a microfluidic device is shown in FIG. 8. Embodiments may be fabricated using a combination of soft lithography and surface micromachining. The PDMS microfluidic layer may be fabricated using soft lithography. At 802, a mold may be fabricated—an approximately 4 in. silicon wafer may be coated with an SU-8 negative photoresist film and the photoresist may be patterned with photolithography. The mold may be treated with trichloro(octyl)silane for approximately 6 hours to increase the surface hydrophobicity for the demolding process. At 804, the device may be molded—PDMS prepolymer and crosslinker may be mixed at approximately a 10:1 ratio, poured on the mold, degassed in vacuum, and cured for approximately 4 hours in an oven at approximately 65° C. At 806, the cured PDMS was then peeled off from the mold, and fluidic inlet, outlet, and auxiliary functionalization ports may be created with a biopsy punch. At 808, separately, the electrical sensor network may be fabricated using a lift-off process. For the sensor fabrication, an approximately 1.2 μm thick NR9 negative photoresist may be spun on an approximately 3 in. by 2 in. glass slide, patterned using a maskless aligner (MLA150, Heidelberg), followed by the evaporation of an approximately 20 nm/480 nm Cr/Au film stack. The sacrificial photoresist may be etched in an acetone bath. At 810, the PDMS layer and the glass substrate may be surface activated in an oxygen plasma environment, aligned under a microscope, and permanently bonded together to form the final device (FIG. 1b).

Human Cancer Cell Line Culture: Mixtures of human cancer cell lines were prepared with different surface antigen expression as control samples to characterize the performance of the device. Three different breast cancer cell lines, MCF7, SK-BR-3, and MDA-MB-231, were cultured in DMEM media supplemented with 10% FBS and maintained under 5% CO2 atmosphere at 37° C. in an incubator. Once 80% confluence reached, cells were detached in a 0.25% trypsin solution, pelleted in a centrifuge, resuspended in 1×PBS, and mixed by gentle pipetting to mechanically dissociate potential cell aggregates. Cell concentration for each cell type was measured with a microscope and different cell lines were mixed at known ratios to create control samples with heterogeneous cell populations.

Human Blood Sample Processing: 1 mL blood samples were collected from healthy donors according to an IRB-approved protocol. To ensure against coagulation, all blood samples were collected in BD EDTA tubes, stored on a rocker at room temperature, and were processed within 6 h of the blood withdrawal. Prior to processing on the assay, erythrocytes were lysed, which greatly outnumber leukocytes. For the assay, erythrocytes would not only hinder contact between the leukocytes and the functionalized device surface but also increase the background noise in electrical signals and decrease the signal-to-noise ratio (SNR) in electrical measurements. To lyse erythrocytes, the blood sample was treated with ammonium-chloride-potassium buffer for ≈15 min and subsequently centrifuged at 350×g for 5 min. The supernatant was removed, and the cell pellet was rinsed twice with PBS to remove erythrocyte residues. The cell pellet was then suspended in PBS with gentle pipetting, filtered using 35 μm nylon mesh incorporated Cell Strainer Snap Cap (Falcon, Corning) to create the leukocyte suspension for the assay.

Electrical Measurement: Cell capture rates were measured for all microfluidic chambers by electrically tracking cell flow on the assay with the integrated electrical sensor network. To detect coded impedance modulations from cells flowing across the microfluidic assay, the device was excited from the common electrode terminal with a 1 V sine wave at 500 kHz supplied from the output of the lock-in amplifier (HF2LI, Zurich Instruments), and the resulting current signals were acquired from the two sensing electrodes. The current signals were first converted into voltage signals using two transimpedance amplifiers, and then subtracted from each other with a differential amplifier to produce a single electrical waveform. The amplitude of the electrical signal was measured with the lock-in amplifier, and sampled to a computer for digital signal processing.

Figure 9:
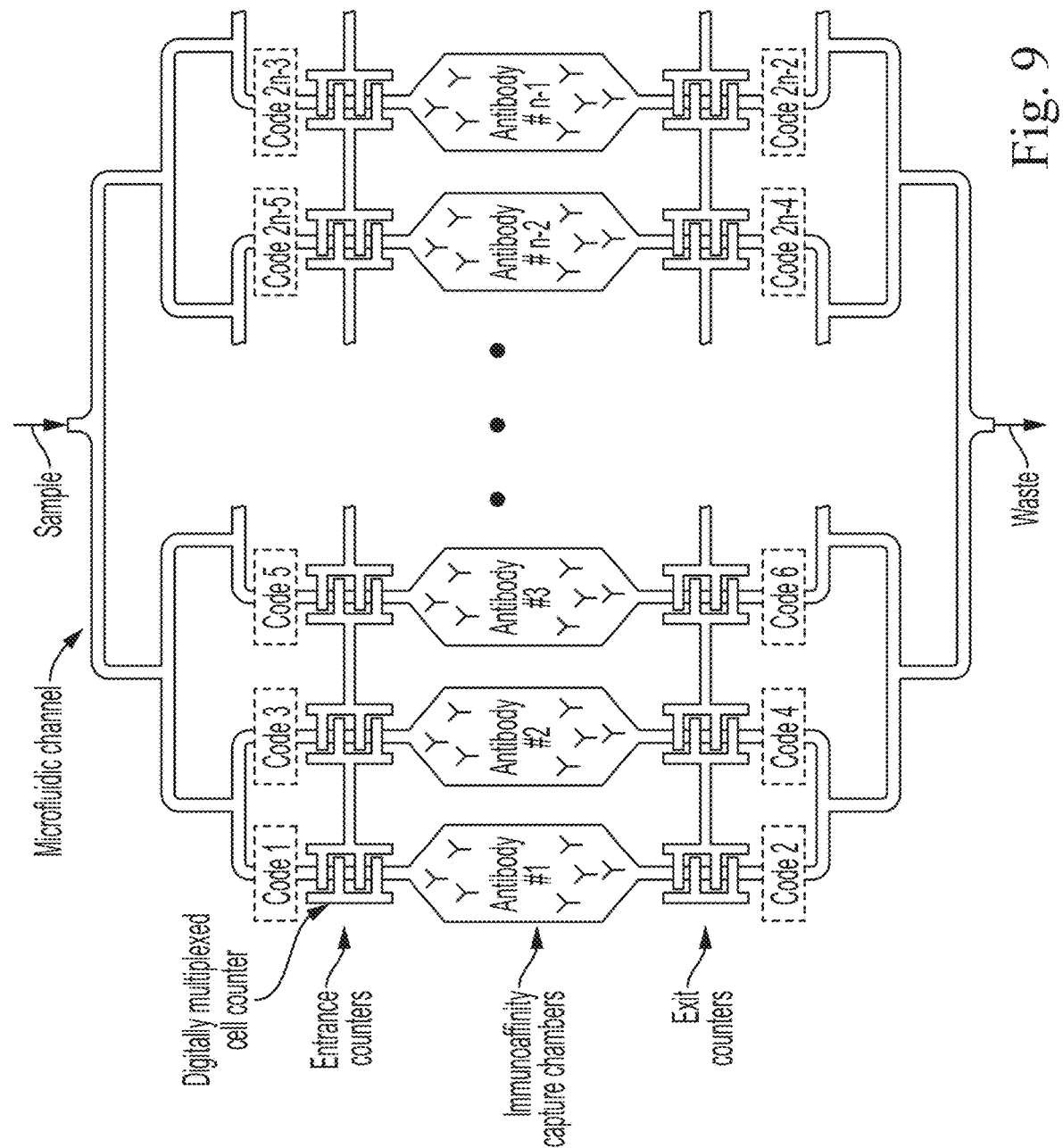
FIG. 9 shows a schematic demonstrating a system and method to carry out label-free electronic immunophenotyping of a cell and/or particle population.

Non-limiting exemplary systems are now described. In some instances the systems can resolve spatial information in affinity-based assays. As shown in FIG. 9, the concept of an integrated electronic platform for label-free immunophenotyping of leukocytes. The proposed system will be a microfluidic chip composed of (1) an array of immunoaffinity-capture chambers (ICCs), each functionalized with a different antibody to target a specific surface antigen of interest, (2) on-chip multiplexed electrical sensors that count blood cells both at the entrance and exit of each ICC to determine the percentage of captured, i.e., antigen-positive subpopulation. An advantage of the system described herein is that it uses an innovative electronic sensing technology to replace microscopic analysis that is required for downstream analysis of conventional microarray immunoassays. This will allow development of a fully integrated device that will be fast, low-cost, portable and more amenable to point-of-care use at mobile and resource-limited settings than existing methods. Such a device will be transformative in monitoring of immune status for both disease diagnosis and prognosis. In addition, the flow rate of the sample can be modulated (even with a feedback loop), to measure instantaneous changes in the capture rates from each channel. This information can be used to assess the level of affinity, which is proportional cell surface antigen density. This can be achieved, because the sensors and devices provided herein also measure flow the speed of the moving particles. In other words, with varying sample flow rate, our technique can provide multidimensional data, which is usually only available using expensive benchtop flow cytometers.

Figure 10:
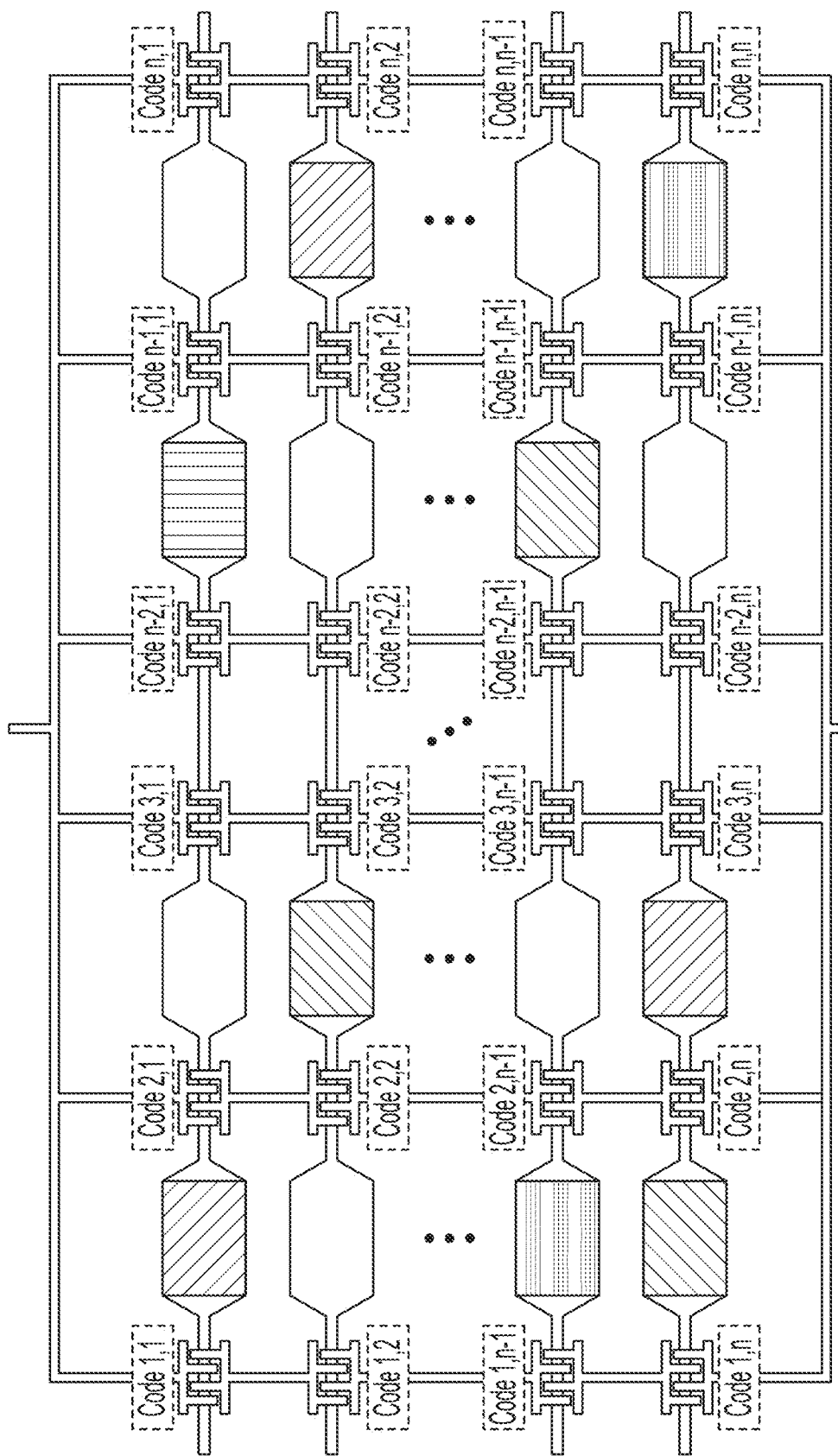
FIG. 10 shows a schematic demonstrating a system and method to carry out label-free electronic immunophenotyping of a cell and/or particle population for multichannel series detection.

For multiplexed detection of surface antigens, we can create devices capable of probing all possible cell phenotypes for antibodies of interest. One approach will be to construct an immunocapture chamber matrix, in which each row contains cascaded chambers with all possible permutations of antibody sequences (FIG. 10). At each node, a sensor producing a distinguishable signal will quantify number of cells transferred between chambers.

Figure 11:
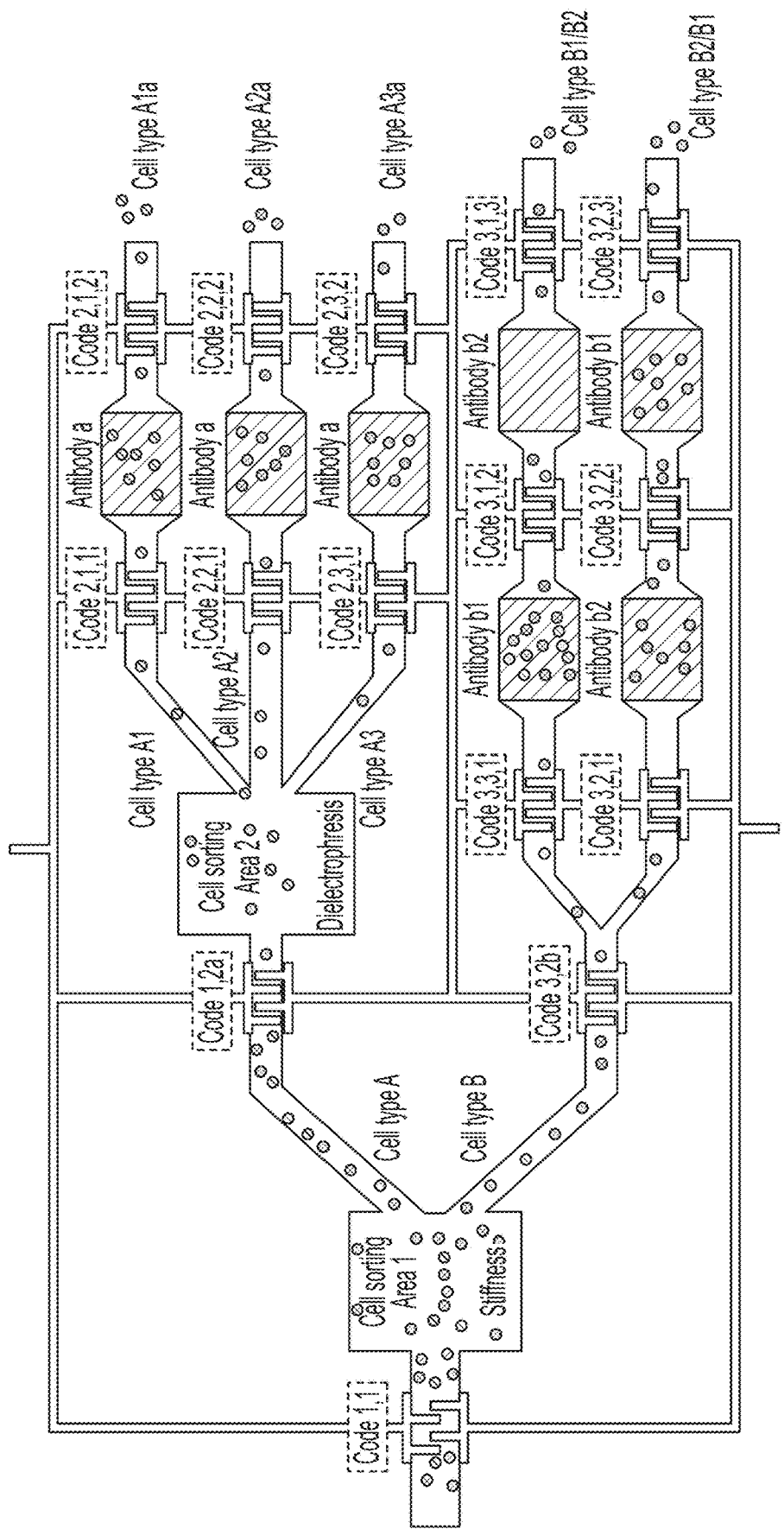
FIG. 11 shows a schematic demonstrating a system and method to carry out label-free electronic multi-modal phenotyping of a cell and/or particle population using multiple fractionation stages.

We can also combine multi-modal manipulation capabilities of microfluidics with a network of on-chip electronic sensors to track cells as they are fractionated on the device (FIG. 11). A device of this sort can electronically analyze cell properties in multiple domains.

Another example where these devices provided herein can be useful is in microfluidic sorting, where cells and particles are spatially mapped to different microfluidic channels based on their properties. Therefore the sensor and devices described herein offers a quantitative readout for sorting based microfluidic devices.

In some embodiments, channels between electrodes can be moved. The devices described herein do not necessarily operate with physical channels. The channels are can be defined by the sensing volumes. As long as the traces are well isolated from each other sensing areas can be laid out to do orthogonal sensing in a single non-compartmentalized microfluidic channel.

Figure 12:
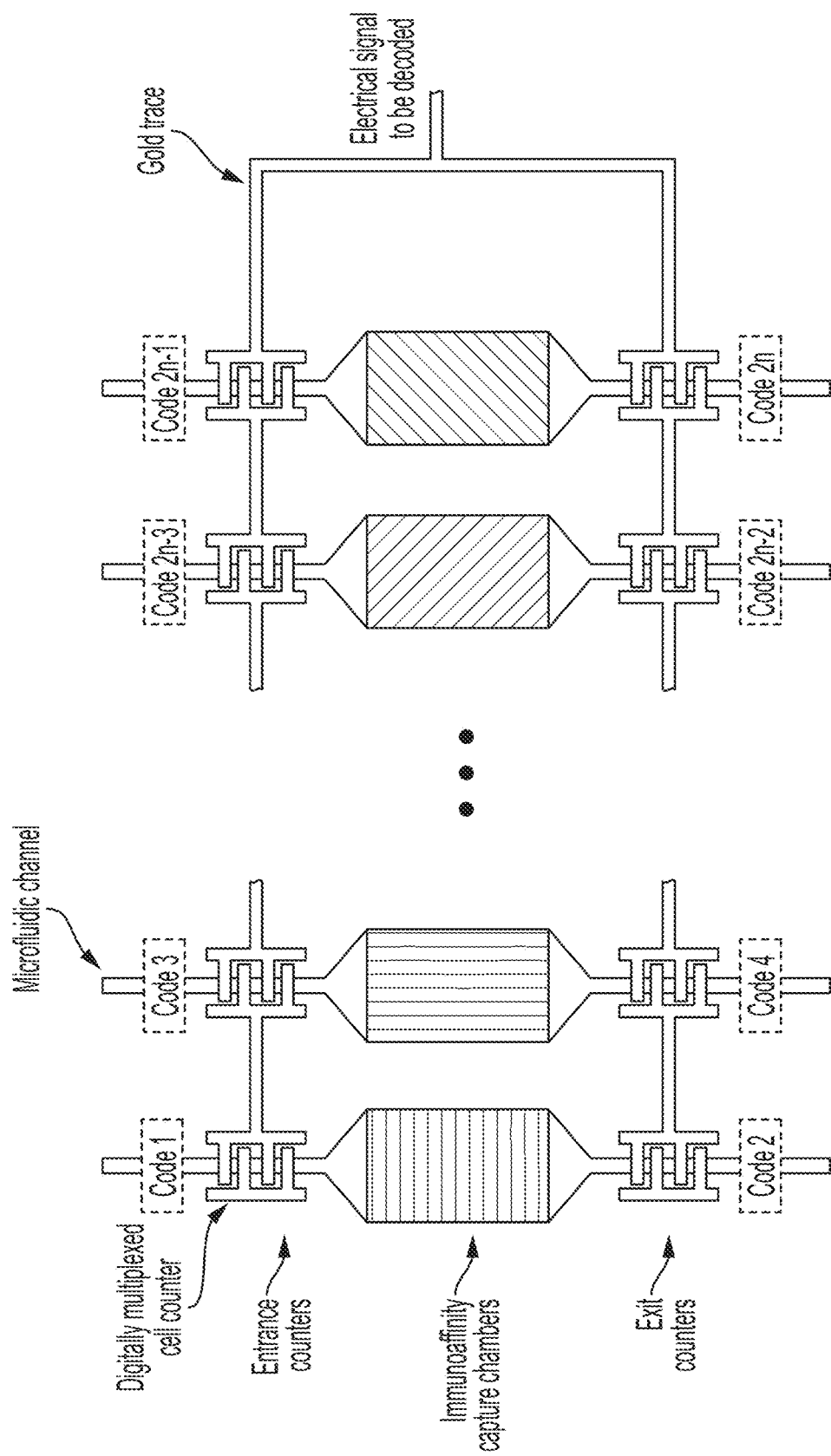
FIG. 12 shows one embodiment of a multiplexed microfluidic device having a coded fluid path.
Figure 13:
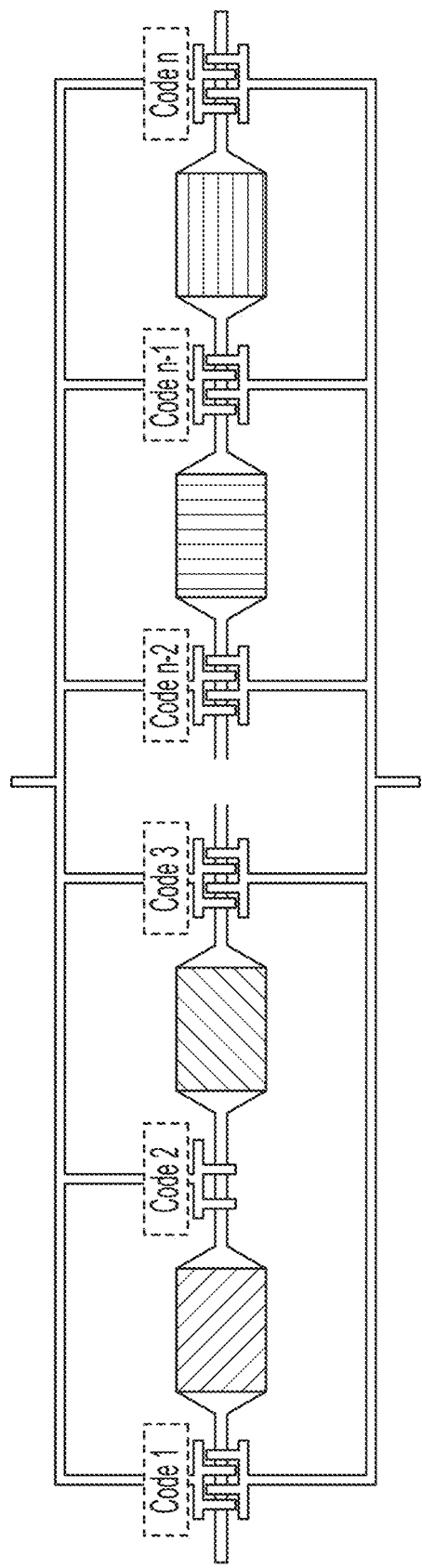
FIG. 13 shows an embodiment of a multiple step particle sorting and antigen and/or label detection process utilizing a multiplexed microfluidic device having a coded fluid path.

Besides parallel structures for cell surface antigen or label recognition, the technology provided herein can be used in series connection devices and mixed connection devices. By using an M×N structure, it is possible to detect and count a series of antigen expression or label on many kinds of cells simultaneously (see e.g. FIGS. 10 and 12-13)

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method of fabricating a device comprising:
fabricating a mold;
forming a portion of the device using the mold;
forming a single fluid inlet port, a single outlet port and a plurality of separate parallel microfluidic paths in the molded portion of the device, said single fluid inlet port connected to the plurality of separate parallel microfluidic paths, each separate microfluidic path configured to transport a plurality of cells wherein each of the separate microfluidic paths comprise a plurality of microfluidic cell capture chambers, wherein at least two of the plurality of microfluidic cell capture chambers are cascaded along each separate microfluidic path, said separate parallel microfluidic paths connected to the single outlet port, wherein the single outlet port discharges a merged output of cells from the plurality of separate parallel microfluidic cell capture chambers;
fabricating an electrical sensor network on a glass substrate, said electrical sensor network comprising a plurality of sensors, wherein each of the plurality of microfluidic cell capture chambers is associated with a corresponding one of the plurality of sensors to detect cells passing into or out of each respective microfluidic cell capture chamber, and wherein the electrical sensor network is further configured to detect as one or more of the plurality of cells enter the device, if any one or more of the plurality of cells pass from one of the at least two of cascaded microfluidic cell capture chambers to another, and if any one or more of the cells is discharged from the device, to provide a count of cells or a distribution of cells captured by all or a portion of the plurality of cascaded microfluidic cell capture chambers;

bonding the glass substrate to the molded portion of the device to form the device, wherein each of the microfluidic cell capture chambers is functionalized by introducing a capture antibody into each microfluidic cell capture chamber.

2. The method of claim 1, wherein fabricating the mold comprises:

patterning a silicon wafer using photolithography; and treating a surface of the patterned silicon wafer to increase surface hydrophobicity for demolding.

3. The method of claim 2, wherein treating the surface of the patterned silicon wafer comprises treating the surface of the patterned silicon wafer with trichloro (octyl) silane for approximately 6 hours.

4. The method of claim 2, wherein forming a portion of the device using the mold comprises:

mixing a polydimethylsiloxane prepolymer and cross-linker;

pouring the mixture on the mold;

curing the polydimethylsiloxane; and peeling cured polydimethylsiloxane from the mold.

5. The method of claim 4, further comprising degassing the poured mixture in vacuum, and the curing is performed for approximately 4 hours in an oven at approximately 65° C.

6. The method of claim 4, further comprising forming auxiliary functionalization ports with a biopsy punch.

7. The method of claim 6, wherein fabricating the electrical sensor network comprises:

forming a patterned photoresist on the glass substrate;

evaporating chromium and then gold into the patterned photoresist; and removing the patterned photoresist.

8. The method of claim 7, wherein the chromium comprises a layer approximately 20 nm thick and the gold comprises a layer approximately 480 nm thick.

9. The method of claim 1, further comprising:

the determining an antigen-positive cell count in each of the plurality of microfluidic cell capture chambers from a mass balance calculation using the electrical sensor network.

10. The method of claim 9, wherein the plurality of sensors are Coulter sensors.

11. The method of claim 1, wherein a first of the at least two of the plurality of microfluidic cell capture chambers cascaded along a first of the plurality of separate microfluidic paths is functionalized with a first capture antibody and a second of the at least two of the plurality of microfluidic cell capture chambers cascaded along the first of the plurality of separate microfluidic paths is functionalized with a second capture antibody, wherein the first capture antibody is not the same as the second capture antibody.

* * * * *